(12) United States Patent
Goble et al.

(10) Patent No.: US 7,594,922 B1
(45) Date of Patent: Sep. 29, 2009

(54) SYSTEM AND METHOD FOR MENISCAL REPAIR THROUGH A MENISCAL CAPSULAR TUNNEL

(75) Inventors: E. Marlowe Goble, Logan, UT (US); Daniel F. Justin, Logan, UT (US); T. Wade Fallin, Hyde Park, UT (US)

(73) Assignee: Medicine Lodge, Inc, Logan, UT (US)

( * ) Notice: Subject to any disclaimer, the term of this patent is extended or adjusted under 35 U.S.C. 154(b) by 582 days.

(21) Appl. No.: 11/102,027

(22) Filed: Apr. 7, 2005

(51) Int. Cl.
*A61F 2/08* (2006.01)
(52) U.S. Cl. .............................. 606/213; 623/14; 623/12
(58) Field of Classification Search ................. 606/215, 606/219, 224, 151, 157, 140, 228, 213, 216; 623/14.12, 13.11, 13.12, 13.13, 13.14; 433/3
See application file for complete search history.

(56) References Cited

U.S. PATENT DOCUMENTS

| | | | |
|---|---|---|---|
| 4,493,323 A * | 1/1985 | Albright et al. | 606/144 |
| 4,597,390 A | 7/1986 | Mulhollan et al. | |
| 4,602,635 A | 7/1986 | Mulhollan et al. | |
| 4,736,746 A | 4/1988 | Anderson | |
| 4,781,190 A | 11/1988 | Lee | |
| 5,002,562 A * | 3/1991 | Oberlander | 606/221 |
| 5,154,189 A | 10/1992 | Oberlander | |
| 5,269,783 A * | 12/1993 | Sander | 606/148 |
| 5,320,633 A | 6/1994 | Allen et al. | |
| 5,467,786 A | 11/1995 | Allen et al. | |
| 5,562,683 A | 10/1996 | Chan | |
| 5,562,687 A * | 10/1996 | Chan | 606/148 |
| 5,702,462 A | 12/1997 | Oberlander | |
| 5,746,754 A | 5/1998 | Chan | |
| 5,928,252 A | 7/1999 | Steadman et al. | |
| 5,954,747 A | 9/1999 | Clark | |
| 6,039,753 A | 3/2000 | Meislin | |

(Continued)

FOREIGN PATENT DOCUMENTS

WO WO03017849 A1 3/2003

(Continued)

OTHER PUBLICATIONS

U.S. Appl. No. 10/983,236, filed Nov. 2004, Stone et al.*

(Continued)

*Primary Examiner*—(Jackie) Tan-Uyen T Ho
*Assistant Examiner*—Christina Lauer
(74) *Attorney, Agent, or Firm*—David W Meibos; Barbara Daniels; Daniel F. Justin

(57) ABSTRACT

A system for open or arthroscopic surgical repair of torn or damaged meniscal tissue has a repair member and an instrument. The repair member is a suture, flexible or rigid implant. The instrument has at a portion that is shaped to slide within a meniscal capsular tunnel. The meniscal capsular tunnel is an opening in the knee soft tissue passing from the anterior side of the knee adjacent to the mensical tissue to the posterior side of the knee in both the medial and lateral directions. The instrument interacts with the repair member to either insert it into the meniscus from the posterior side, or to facilitate securing of the repair member so that the repair member holds the meniscal tissue together on either side of a meniscal tear to foster healing of the damaged tissue.

14 Claims, 20 Drawing Sheets

U.S. PATENT DOCUMENTS

| | | |
|---|---|---|
| 6,368,335 B1 | 4/2002 | Chan |
| 6,626,916 B1 | 9/2003 | Yeung et al. |
| 6,629,984 B1 | 10/2003 | Chan |
| 6,663,633 B1 | 12/2003 | Pierson, III |
| 6,767,352 B2 | 7/2004 | Field et al. |
| 2002/0002374 A1 | 1/2002 | Barreiro et al. |
| 2002/0019649 A1 | 2/2002 | Sikora et al. |
| 2002/0169452 A1 | 11/2002 | Tormala et al. |
| 2002/0169477 A1 | 11/2002 | Demopulos et al. |
| 2002/0193811 A1 | 12/2002 | Chan |
| 2003/0078600 A1 | 4/2003 | O'Quinn et al. |
| 2003/0078617 A1 | 4/2003 | Schwartz et al. |
| 2003/0097148 A1 | 5/2003 | Valimaa et al. |
| 2003/0204194 A1 | 10/2003 | Bittar |
| 2004/0002734 A1* | 1/2004 | Fallin et al. ............ 606/232 |
| 2004/0015186 A1 | 1/2004 | Bittar |
| 2004/0133238 A1 | 7/2004 | Cerier |
| 2004/0147957 A1 | 7/2004 | Pierson |
| 2004/0153103 A1 | 8/2004 | Schwartz et al. |
| 2004/0176802 A1 | 9/2004 | Skiba et al. |
| 2004/0186515 A1 | 9/2004 | Rosenblatt |
| 2004/0199184 A1 | 10/2004 | Topper et al. |
| 2004/0199185 A1 | 10/2004 | Davignon |
| 2004/0267270 A1 | 12/2004 | Jacobs et al. |
| 2004/0267276 A1 | 12/2004 | Camino et al. |
| 2005/0027307 A1 | 2/2005 | Schwartz et al. |
| 2005/0033363 A1 | 2/2005 | Bojarski et al. |
| 2005/0043747 A1 | 2/2005 | Field et al. |
| 2005/0049617 A1 | 3/2005 | Chatlynne et al. |

FOREIGN PATENT DOCUMENTS

| | | |
|---|---|---|
| WO | WO2004034913 A1 | 4/2004 |
| WO | WO2005018467 A2 | 3/2005 |

OTHER PUBLICATIONS

Hwan Ahn, Jin. M.D., Joon-Ho Wang, M.D., and Irvin Oh, M.D. "Modified Inside-Out Technique for Meniscal Repair" *Arthroscopy* Jul.-Aug. 2004: pp. 178-182.

Morgan, Craig D. M.D., "The All-Inside Meniscus Repair" *Arthroscopy* 1999: pp. 120-125.

Newman, Alan P. M.D., "Arthroscopic Meniscal Repair Insid-Out Technique" *Operative Techniques in Sports Medicine* Jul. 1994: pp. 177-189.

Morgan, Craig D. M.D., "All-Inside Arthroscopic Meniscus Repair" *Operative Techniques in Sports Medicine*, Jul. 1994: pp. 201-207.

Arciero, Robert A. LTC, MC and Taylor, Maj MC. "Inside-Outside and All-Inside Meniscus Repair: Indications, Techniques, and Results" *Operative Techniques in Othopedics*, Jan. 1995: pp. 58-69.

Jin Hwan Ahn, M.D, Ph.D., Seung-Ho Kim, M.D., Jae Chul Yoo, M.D., and Joon Ho Wang, M.D., "All-Inside Suture Technique Using Two Posteromedial Portals in a medical Meniscus Posterior Horn Tear" *Arthroscopy*: Jan. 2004: pp. 101-108.

W. Dilworth Cannon, Jr, M.D., "Arthroscopic Meniscal Repair" *The American Journal of Knee Surgery*, Summer 1996: pp. 137-143.

Grae,e C. Brown, FRACS, Thomas D. Rosenber, M.D., Kathleen T. Diffner, "Inside-Out Meniscal Repair Using Zone-Specific Instruments" *The American Journal of Knee Surgery*, Summer. 1996: pp. 144-150.

\* cited by examiner

SYSTEM AND METHOD FOR MENISCAL REPAIR THROUGH A MENISCAL CAPSULAR TUNNEL

CROSS-REFERENCE TO RELATED APPLICATIONS

The following disclosures are incorporated herein by reference:

U.S. application Ser. No. 10/459,375, filed Jun. 11, 2003 now U.S. Pat. No. 7,150,757, and is entitled LINE LOCK SUTURE ATTACHMENT SYSTEMS AND METHODS;

U.S. application Ser. No. 10/936,376, filed Sep. 7, 2004, and is entitled ADJUSTABLE LINE LOCKS AND METHODS;

U.S. application Ser. No. 10/942,275, filed Sep. 15, 2004, and is entitled LINE LOCK THREADING SYSTEMS AND METHODS; and U.S. application Ser. No. 11/001,866, filed Dec. 1, 2004, and is entitled LINE LOCK SUTURE ATTACHMENT SYSTEMS AND METHODS.

BACKGROUND OF THE INVENTION

1. The Field of the Invention

The present invention relates generally to restoration of damaged or torn meniscal tissue in articulating joints of the body, and more specifically, to restoration of a knee meniscal tissue.

2. The Relevant Technology

The meniscus of the knee is a crescent shape of fibrocartilage interposed between the condyles of the femur and the tibia on the lateral and medial sides of the knee. The menisci are integral components of the complex biomechanics of the knee and possess unique physical and biomechanical properties. Due to trauma, disease, or wear, local tears or damage can be formed within the meniscal structure. Such defects can cause discomfort for a patient and left untreated, can accelerate wear of the articular cartilage on both the tibia and the femur.

Accordingly, several treatments have been developed to address repairing torn meniscal tissue. These treatments typically involve holding the torn or damaged tissue together with an implant placed in the vascular area of the meniscus long enough for the mensical tissue to heal itself. These implants are sutures, bioabsorbable fixation devices, biological glues or autologus reconstituted tissue created by applying an energy source to the damaged tissue such as a Laser or ultrasonic tissue ablation energy source. Via various methods known in the art, the mensical tissue is regenerated over the area held together by the implant and once healed the meniscus tend to regain function allowing the knee to mobilize normally.

Unfortunately, traditional meniscal repair systems do not allow for optimum placement of the implant. Surgeons have traditionally accessed the damaged mensical tissue from the interior cavity of the knee, or made incisions adjacent to the damaged tissue on the outside of the knee, then cut through the skin, fascia, and knee capsule in a direct approach to access the torn meniscus with repair implants. This invasive approach is less common since it is technically demanding, requiring avoidance of the complex neurovascular structures such as the peroneal nerve, popliteal nerve, saphenous nerve and popliteal artery. Additionally, such an approach can increase the patient's discomfort and recovery time. Accordingly, there is a need for less invasive procedures that facilitate optimal implant placement to expedite recovery and minimize patient discomfort.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
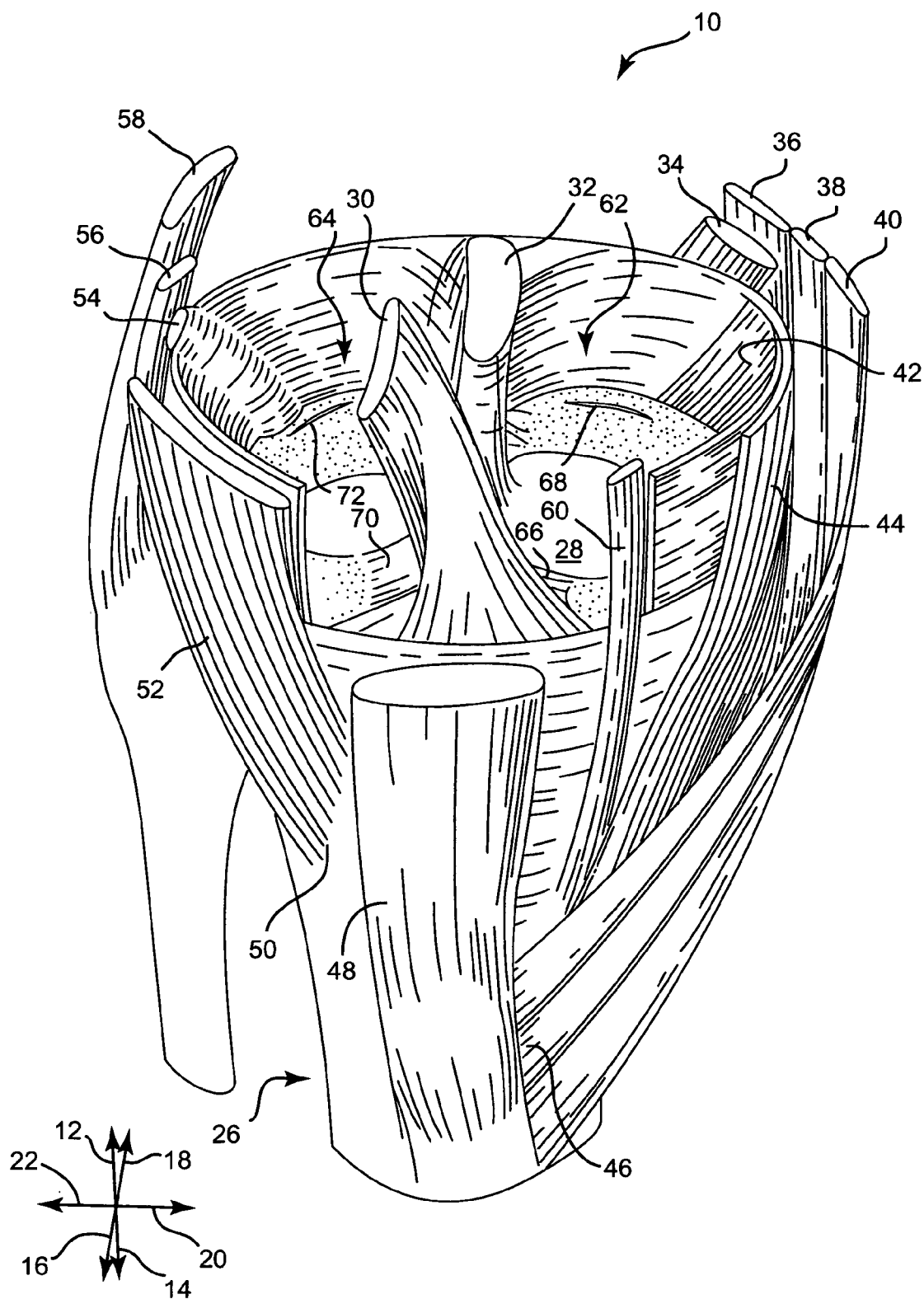
FIG. 1 is an anterior cut-away view of the major skeletal, ligamentus, tendonous and muscular structures of the knee.

The present invention relates to systems for repairing torn or damaged meniscal tissue. Those of skill in the art will recognize that the systems and methods described herein may be readily adapted for repair of other types of tissue. Various embodiment of the invention will be shown and described in connection with FIGS. 1 through 20B, as follows.

In this application, a "meniscal capsular tunnel" refers to any type of passageway naturally existing, or formed by dilating a potential space, within the knee capsuloligamentous system encapsulating the knee joint. The knee capsular fibers are exterior to the medial meniscus and lateral meniscus. The knee capsular fibers typically include, but are not limited to, the discrete ligamentus fibrous membrane that includes the pars profonda (deep MCL), femoromeniscalis meniscotibialis, and posterior oblique ligament. The knee capsular tissue fibers proximally attach circumferentially to the femur and distally attach circumferentially to the tibial margin except for areas where popliteal ligaments and tendons enter the knee joint.

On the medial side of the knee the tissues external to the knee capsular tissue fibers include the medial collateral ligament, the superficial medial collateral ligament, the medial superficial fascial layer, the medial deep fascial layer, the sartorius muscle, the gracilis muscle, the semitendinosus muscle, the semimembranosus muscle, the medial longitudinal patellar retinaculum, the oblique popliteal ligament, other structural tissue layers of the medial capsuloligamentous system, fat, and neurovascular structures.

On the lateral side of the knee, the tissues external to the knee capsular tissue fibers include the lateral collateral ligament, the biceps femoris tendon, the illiotibial band, the popliteus tendon, other structural tissue layers of lateral capsuloligamentous system, the lateral superficial fascial layer, the lateral deep fascial layer, fat, and neurovascular structures.

According to preferred methods, separate tissues must simply be spread apart to provide the meniscal capsular tunnel. The meniscal capsular tunnel may advantageously be formed by dilating a potential space having a relatively large potential cross sectional area. However, the phrase "meniscal capsular tunnel" also includes spaces formed by bifurcation of a single tissue.

An "adjacent meniscal capsular tunnel" is a type of meniscal capsular tunnel that more specifically refers to a passageway formed by dilating the potential space between a first tissue immediately adjacent to the meniscus and a second tissue immediately exterior to the first tissue to facilitate implantation of the repair member in the meniscus. The first tissue may be the pars profonda (deep MCL), and the second tissue may be the superficial MCL. However, the tissues that bound the dilated space depend on the particular anatomy of the patient's knee and the location of the portion of the adjacent meniscal capsular tunnel with respect to the knee. An adjacent meniscal capsular tunnel may be bounded by a variety of different tissues as it extends around the periphery of the meniscus.

In this application, the term "instrument" is broadly defined as any item that can be used to help carry out a surgical procedure. An instrument may, in some instances, be allowed to remain in the body after completion of the surgical procedure. The term "adjacent" does not necessarily refer to two objects that are in contact or near-contact with each other. Rather, adjacent objects are simply near each other. "Immediately adjacent" objects are positioned such that at least a portion of the space between the two objects is not occupied by any other solid object.

In this application, "implantation" of an object into the body refers to insertion of the object into its proper location within the body, and securing the object to ensure that it remains in place. Thus, an object that has been positioned within the body, but will not remain in the body and positioned to perform its desired function immediately following the closure of the surgical incision, has not been "implanted." Thus, bioabsorbable devices left in the body and autologous tissue manipulated by the surgeon such as fibrin glues, other biological glues or autologous reconstituted tissue created by applying an energy source to the damaged tissue such as a Laser or ultrasonic tissue ablation energy source are all considered "implanted". However, insertion of the object and securement of the object may be performed in a single step, if the object is positioned in such a way that, once positioned, it will remain in place without any further manipulation. A "delivery interface" is any feature designed to facilitate insertion of an object (e.g., an implant) into its proper location within the body. A "retention interface" is any feature designed to help secure the object.

In this application, a "staple" is an elongated member, at least a portion of which is able to pass through tissue. A staple has more rigidity than a suture, with ends that are securable to restrict motion of the staple with respect to the tissue through which it passes. A "barbed" structure has a protrusion shaped to be insertable through an aperture along one direction, and to resist withdrawal from the aperture along the opposite direction.

In this application, "within the knee" means within the space bounded by the outer layer of skin surrounding the knee. A "tunnel" refers to a space between bodily tissues. Motion through a tunnel refers to motion generally parallel to the tissues that define the tunnel, rather than motion through the tissues.

In this application, a first object that is "exterior" to a second object refers to the fact that at least a portion of the second object is positioned between the first object and an axis or geometric center relevant to the first and second objects. In relation to the human body, such an axis or geometric center may be the axis of a limb of the body, the center of a joint, or the like. Similarly, the second object is "interior" to the first object if at least a portion of the second object is positioned between the first object and the axis or geometric center.

When used to refer to anatomical features, "proximal" means closer to the center of the body, and "distal" means further from the center of the body. When used to refer to an object such as an instrument, a "proximal end" is an attached, secured, or grasped end, and a "distal end" is a protruding or extending end. A "potential space" within the body is a region between tissues that can be "dilated," or expanded.

In this application,

Referring to FIG. 1, an anterior cut-away view illustrates the major skeletal, ligamentus, tendonous and muscular structures of a knee 10. As shown, the knee 10 has a cephalad direction 12, a caudal direction 14, an anterior direction 16 (generally out of the page), a posterior direction 18 (generally into the page), a medial direction 20, and a lateral direction 22. The directions 12, 14, 16, 18, 20, 22 form a coordinate system with three axes that are perpendicular to each other.

The knee 10 has a variety of ligaments, many of which cooperate to define a capsule of the knee 10 that retains fluid to facilitate articulation of the knee 10. Many of the ligaments are attached proximally to a femur (not shown) and distally to a tibia 26 having a plateau 28. An anterior cruciate ligament (ACL) 30 and a posterior cruciate ligament (PCL) 32 extend through the space within the capsule of the knee 10. On the medial/posterior, medial, and medial/anterior sides of the knee 10, there is a semimembranosus muscle (Sm) 34, semitendinosus muscle (St) 36, a gracilis muscle (Gr) 38, a sartorius muscle (Sa) 40, posterior oblique collateral ligament (POL) 42, and a medial collateral ligament (MCL) 44. On the anterior and anterior/lateral sides of the knee 10, there is a pes anserinus (PA) 46, a patellar ligament (PL) 48, a tubercle of Gerdy (TG) 50, and an iliotibial tract (ITT) 52. On the posterior/lateral side of the knee 10, there is a popliteus tendon (PT) 54, a lateral collateral ligament (LCL) 56, and a biceps tendon (BT) 58. A medial longitudinal patellar retinaculum (MLPR) 60 extends along the anterior/lateral side of the knee 10.

As shown, the knee 10 includes a medial meniscus (MM) 62, and a lateral meniscus (LM) 64. The menisci 62, 64 are cartilaginous structures that facilitate articulation of the femur (not shown) and the tibia 28 in a combination of relative rolling and sliding motions. The medial meniscus 62 is generally horseshoe-shaped, with ends secured to the plateau 28 of the tibia 26 by a pair of ligaments 66 that permit the medial end of the medial meniscus 62 to move along the cephalad and caudal directions 12, 14 to further enhance and facilitate articulation. As shown in FIG. 1, the medial meniscus 62 has a tear 68 extending along the posterior portion of the medial meniscus 62 at a relatively common location for meniscal injury.

The lateral meniscus 64 is similarly horseshoe-shaped, with ends secured to the plateau 28 by a pair of ligaments 70 that permit the lateral end of the lateral meniscus 64 to move along the cephalad and caudal directions 12, 14 to further enhance and facilitate articulation. As shown, the lateral meniscus 64 has a tear 72 extending along a posterior portion of the lateral meniscus 64 at a relatively common location for meniscal injury.

A variety of ligamentomuscular structures (only some of which are shown) and neurovascular structures (not shown) are positioned exteriorly of, and particularly posteriorly of, the menisci 62, 64. Such structures extend generally exteriorly of the tissues illustrated in FIG. 1. According to traditional meniscal repair methods, such structures must often be retracted to provide access to the posterior, medial, or lateral sides of the menisci 62, 64 without damaging the ligamentomuscular and neurovascular structures. Unfortunately, such retraction adds significantly to the complexity of the surgical procedure. Furthermore, such retraction is somewhat invasive, and therefore adds to the required recovery time for meniscal repair. Advantageously, the present invention utilizes dilation of potential spaces within the knee 10 to avoid the need to retract the ligamentomuscular and neurovascular structures that extend posteriorly, medially, or laterally of the menisci 62, 64.

Figure 2:
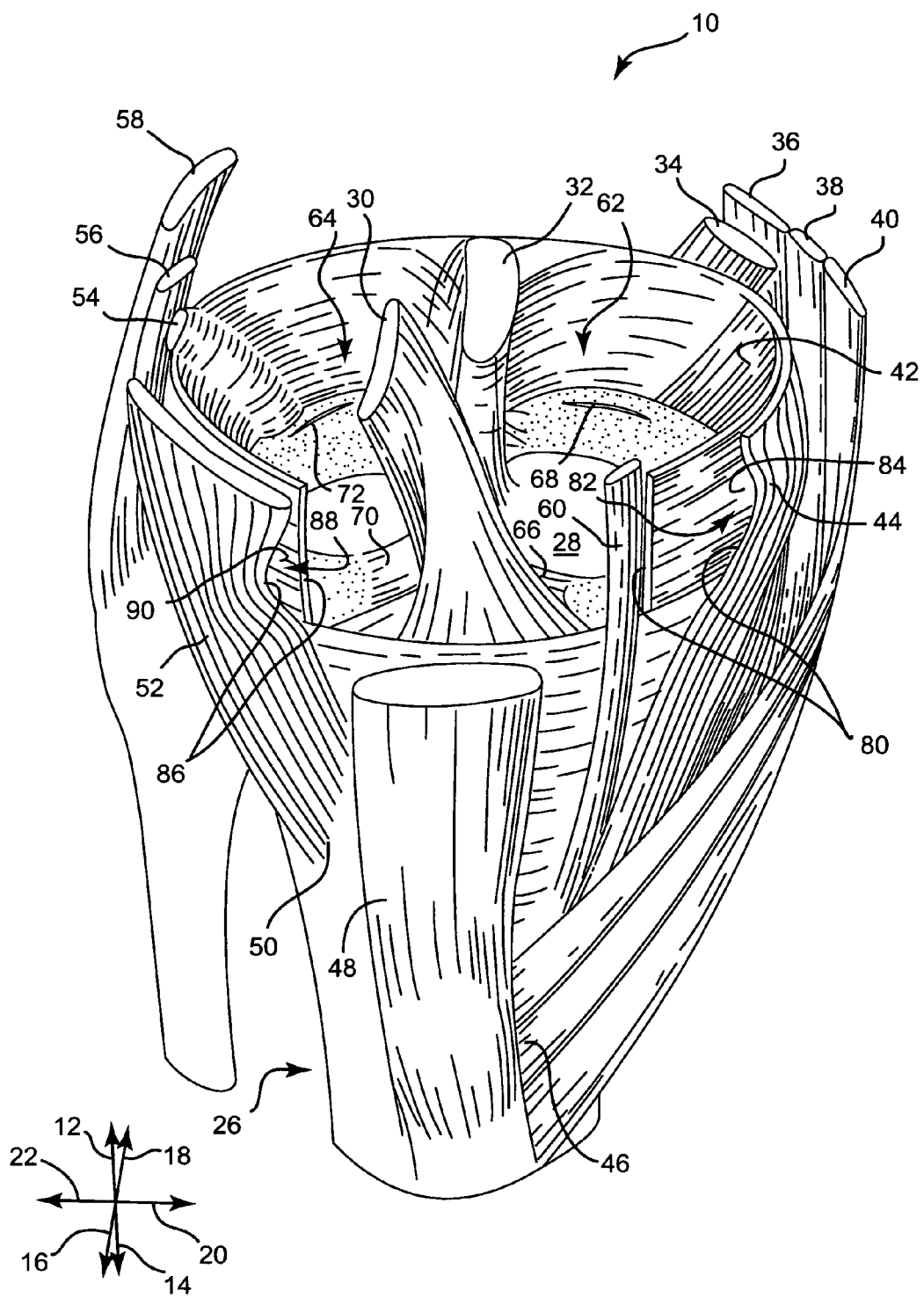
FIG. 2 is an anterior cut-away view as in FIG. 1 showing an opening to the medial meniscal capsular tunnel and the lateral meniscal capsular tunnel.

Referring to FIG. 2, an anterior cut-away view illustrates formation of two meniscal capsular tunnels that provide enhanced access to the tears 68, 72 of the menisci 62, 64.

More precisely, on the medial side, a potential space between medial tissues has been dilated, thereby forming displaced portions 80 of the medial tissues. The dilated space is a medial meniscal capsular tunnel (MMCT) 82 that may extend around the medial end of the medial meniscus 62 to reach a position adjacent to the tear 68 on the posterior side of the medial meniscus 62. Dilation of the potential space between the medial tissues may be carried out by inserting the distal end of an instrument (not shown in FIG. 2) into an anterior portion 84 of the MMCT and actuating the distal end around the medial end of the medial meniscus 62. Such an instrument may be inserted into the anterior portion 84 through an incision (not shown) that may be formed on the anterior side of the knee 10. Intervening tissues between the incision and the anterior portion 84 may need to be removed to provide access to the anterior portion 84.

On the lateral side, a potential space between lateral tissues has been dilated, thereby forming displaced portions 86 of the lateral tissues. The dilated space is a lateral meniscal capsular tunnel (LMCT) 88 that may extend around the lateral end of the lateral meniscus 64 to reach a position adjacent to the tear 72 on the posterior side of the lateral meniscus 64. Dilation of the potential space between the lateral tissues may be carried out by inserting the distal end of an instrument (not shown in FIG. 2) into an anterior portion 90 of the LMCT and actuating the distal end around the lateral end of the lateral meniscus 64. Such an instrument may be inserted into the anterior portion 90 through an incision (not shown) that may be formed on the anterior side of the knee 10. Intervening tissues between the incision and the anterior portion 90 may need to be removed to provide access to the anterior portion 90.

Figure 3:
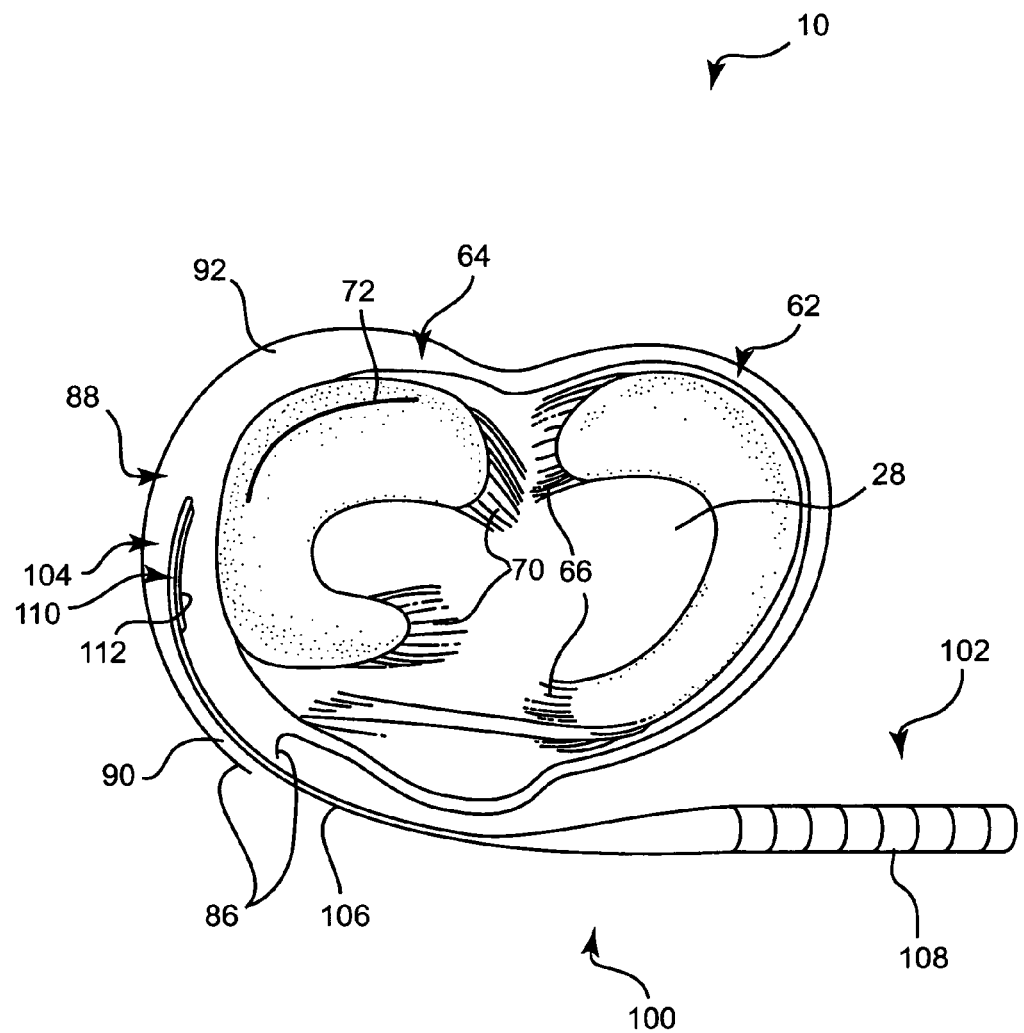
FIG. 3 is a cephalad section view of the knee, showing the medial meniscus, the lateral meniscus with a tear in the posterolateral peripheral meniscal region and a securing instrument with a distal end placed in the lateral meniscal capsular tunnel.

Referring to FIG. 3, a cephalad section view illustrates the knee 10, showing the medial meniscus 62 (with the tear 68 removed for clarity) and the lateral meniscus 64 with the tear 72. FIG. 3 and subsequent Figures focus on the exemplary tear 72 in the lateral meniscus 64. However, the structures and methods set forth below apply equally to tears formed in the posterior, medial, or lateral sides of the lateral meniscus 64 or the medial meniscus 62. The tear 72 is a circumferential peripheral tear, however other tears shapes know in the art that are not shown such as radial tears, bucket handle tears, parrot beak tears, partial thickness tears and vertical tears can be repaired using the systems and methods described herein. Additionally, the structures and methods set forth below may also be used to effect repair of other bodily tissues, aside from the menisci of the knee.

As shown, in addition to the anterior portion 90, the LMCT 88 has a posterior portion 92 positioned posteriorly of the tear 72 of the lateral meniscus 64. The LMCT 88 provides communication between the anterior portion 90 and the posterior portion 92 so that an object, such as the end of a securement instrument 100, may be inserted into the anterior portion 90 and moved along the LMCT 88 to reach the posterior portion 92.

The securement instrument 100, or instrument 100, is designed to help secure a repair member (not shown in FIG. 3) to the lateral meniscus 64 to help repair the tear 72. The securement instrument 100 has a proximal end 102, a distal end 104, and an intermediate portion 106 that spans the distance between the proximal end 102 and the distal end 104. The proximal end 102 has a handle 108 shaped to be grasped in the hand of a surgeon. The distal end 104 has a retention interface 110 designed to facilitate securement of the repair member to the lateral meniscus 64 in a manner that will be shown and described in greater detail in connection with FIGS. 4 through 6.

The retention interface 110 may include a pad 112. The pad 112 may have any of a variety of configurations designed to retain suture ends, or suture ends with needles or barbs attached. The pad 112 may be formed of an elastomeric material, a woven mesh, a formed receptor, a sticky adhesive, a magnetic material, or the like. In the alternative, the pad 112 may be replaced with a different structure designed to receive and retain suture ends. Such a structure may be a gripping clamp or the like.

In order to reach the position shown in FIG. 3, the distal end 104 may first be inserted into an incision in the patient's skin adjacent to the anterior portion 90 of the LMCT 88. The distal end 104 may then be pushed gently between the lateral tissues shown in FIG. 2 (or other tissues) to dilate the corresponding potential space, thereby forming the anterior portion 90 of the LMCT 88. Continued motion of the distal end 104 along the LMCT 88 may cause dilation of the potential space immediately in front of the distal end 104, so that the LMCT 88 is formed to accommodate passage of the distal end 104 until the distal end 104 reaches the posterior portion 92. Arthroscopy, fluoroscopy, or other known methods may be used to ensure that the distal end 104 moves along the intended path. Indeed, such methods may be used in conjunction with any of the procedures described in this application. Alternatively, the pad 112 may have embedded in it a light source that can illuminate from the distal end 104 through tissues to help the surgeon guide the distal end 104.

The central portion 106 of the instrument 100 may be flexible so that the central portion 106 is able to follow the contour of the LMCT 88. However, the central portion 106 may also have sufficient rigidity to transmit pressure along the axis of the handle 108 to the distal end 104 so that exertion of axial pressure on the handle 108 causes the distal end 104 to further dilate the lateral tissues. In the alternative to usage of the instrument 100 to form the LMCT 88, a different instrument (not shown), preferably with a blunt distal end, may be used to dilate the potential space between the lateral tissues to form the LMCT 88 to facilitate insertion of the distal end 104. A blunt distal end facilitates dilation of the tissues without puncturing them.

Figure 4A:
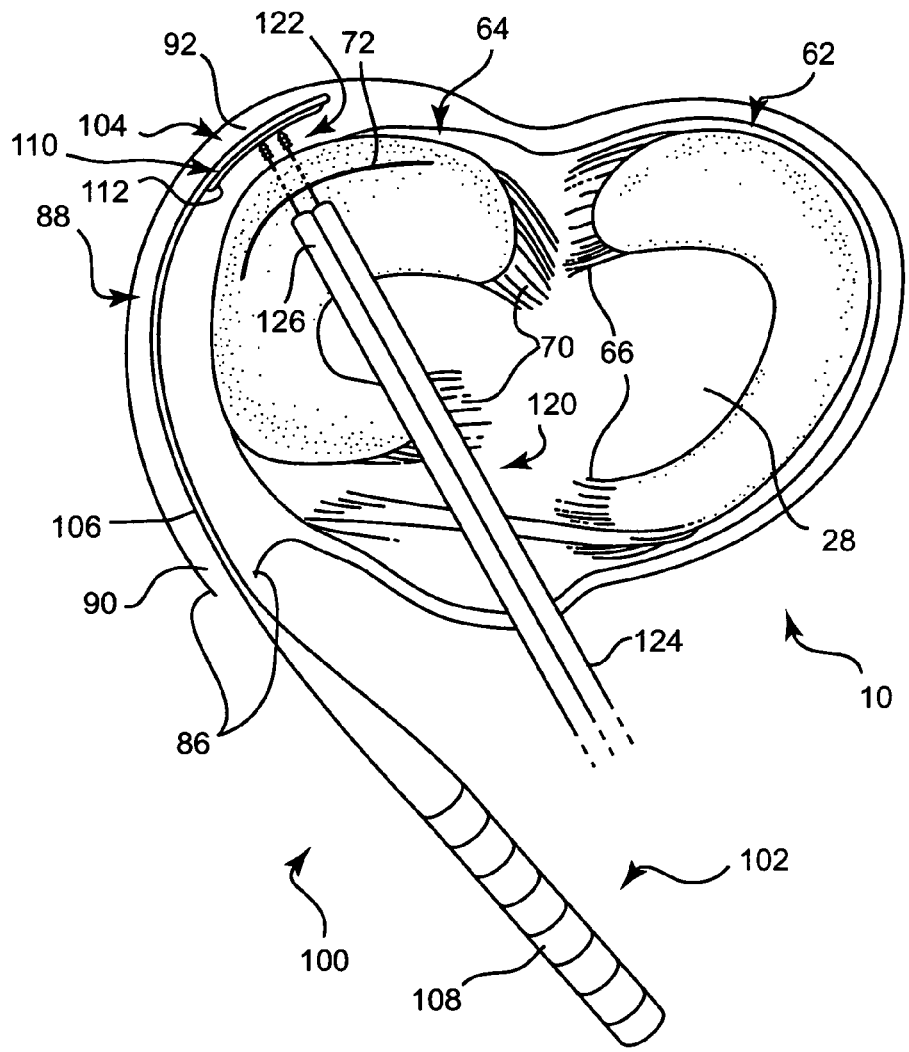
FIG. 4A is a cephalad section view of the knee, showing a delivery instrument inserted through the interior of the knee, with a distal end of the delivery instrument positioned proximate the tear, with the distal end of the securing instrument actuated further into the lateral meniscal capsular tunnel.

Referring to FIG. 4A, a cephalad section view of the knee 10 illustrates usage of the instrument 100 in conjunction with a delivery instrument 120 to implant a repair member 122 in the lateral meniscus 64. The delivery instrument 120 is used to deliver the repair member 122 by passing it through the lateral meniscus 64. The delivery instrument 120 may have a proximal end 124 designed to be grasped by a surgeon, and a distal end 126 insertable into the interior space of the knee 10, proximally of the lateral meniscus 64. Like the instrument 100, the delivery instrument 120 may be inserted into the knee 10 through an incision formed in the skin of the anterior side of the knee 10. The delivery instrument 120 may be cannulated, with two parallel lumens (not visible), each of which has a generally circular cross sectional shape. The lumens may be entirely separate, or may be in communication with each other through a central channel.

In FIG. 4A, the distal end 104 of the instrument 100 has been moved into the posterior portion 92 of the LMCT 88. The pad 112 of the retention interface 110 is positioned posteriorly of the tear 72 to help secure the repair member 122, as will be described subsequently.

Figure 4B:
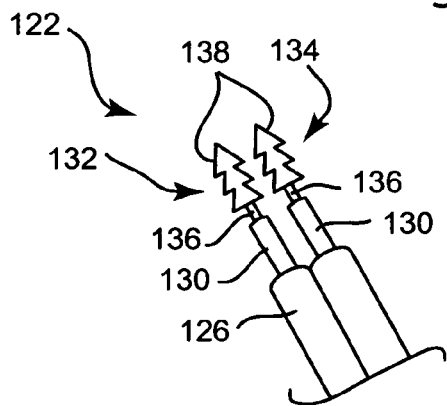
FIG. 4B is an enlarged cephalad view of the knee, showing the distal end of the delivery instrument in isolation, illustrating first and second ends of a suture in the process of being actuated toward the lateral meniscus via push rods.

Referring to FIG. 4B, an enlarged cephalad view of the knee 10 illustrates the distal end of the delivery instrument 120 and the repair member 122. Additionally, FIG. 4B illustrates push rods 130 that may be used to facilitate insertion of the repair member 122 into the tissue of the lateral meniscus 64.

As shown, the repair member 122 has a first end 132 and a second end 134. The repair member 122 is formed of a length of suture 136 attached at both ends with barbs 138 to form the first end 132 and the second end 134. The barbs 138 need not remain in the knee 10, and therefore need not be formed of biocompatible or bioabsorbable materials. At least the end of each of the push rods 130 may have a generally tubular shape that encircles a portion of the length of suture 136 and fits within the corresponding lumen (not visible) of the delivery instrument 120.

When the distal end 126 of the delivery instrument 120 is positioned such that the barbs 138 are in place to enter the lateral meniscus 64 interiorly of the tear 72, the push rods 130 may be actuated to push the barbs 138 through the tissue of the lateral meniscus 64. The push rods 130 are moved along the axis of the insertion instrument 120 until the barbs 138 have passed into the lateral meniscus 64, through the tear 72, and out of the lateral meniscus 64 on the posterior side. The push rods 130 are further actuated to push the barbs 138 into the pad 112 so that the barbs 138 embed themselves in the pad 112. Impingement in the pad 112 prevents damage to any of the ligamentomuscular or neurovascular structures positioned posteriorly of the posterior portion 92 of the LMCT 88. Once the barbs 138 have been embedded in the pad 112, the push rods 130 may then be retracted.

Figure 4C:
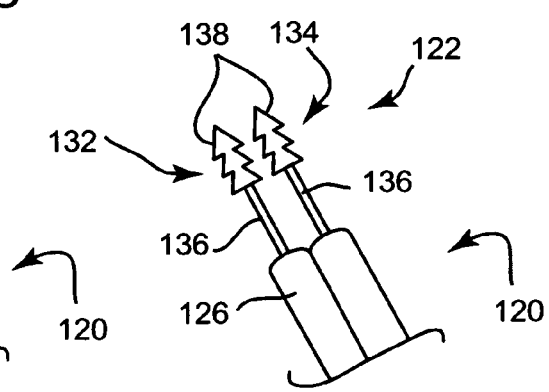
FIG. 4C is an enlarged cephalad view of the knee, showing the distal end of the delivery instrument in isolation, illustrating the first and second ends of the suture after insertion through at least a portion of the lateral meniscus and retraction of the push rods.

Referring to FIG. 4C, an enlarged cephalad view of the knee 10 illustrates the distal end of the delivery instrument 120 and the repair member 122, with the push rods 130 retracted. The ends 134, 136 have been inserted through the lateral meniscus 64 and embedded in the pad 112; thus, the delivery instrument 120 has performed its function. The delivery instrument 120 may then be retracted from the knee 10.

Figure 5:
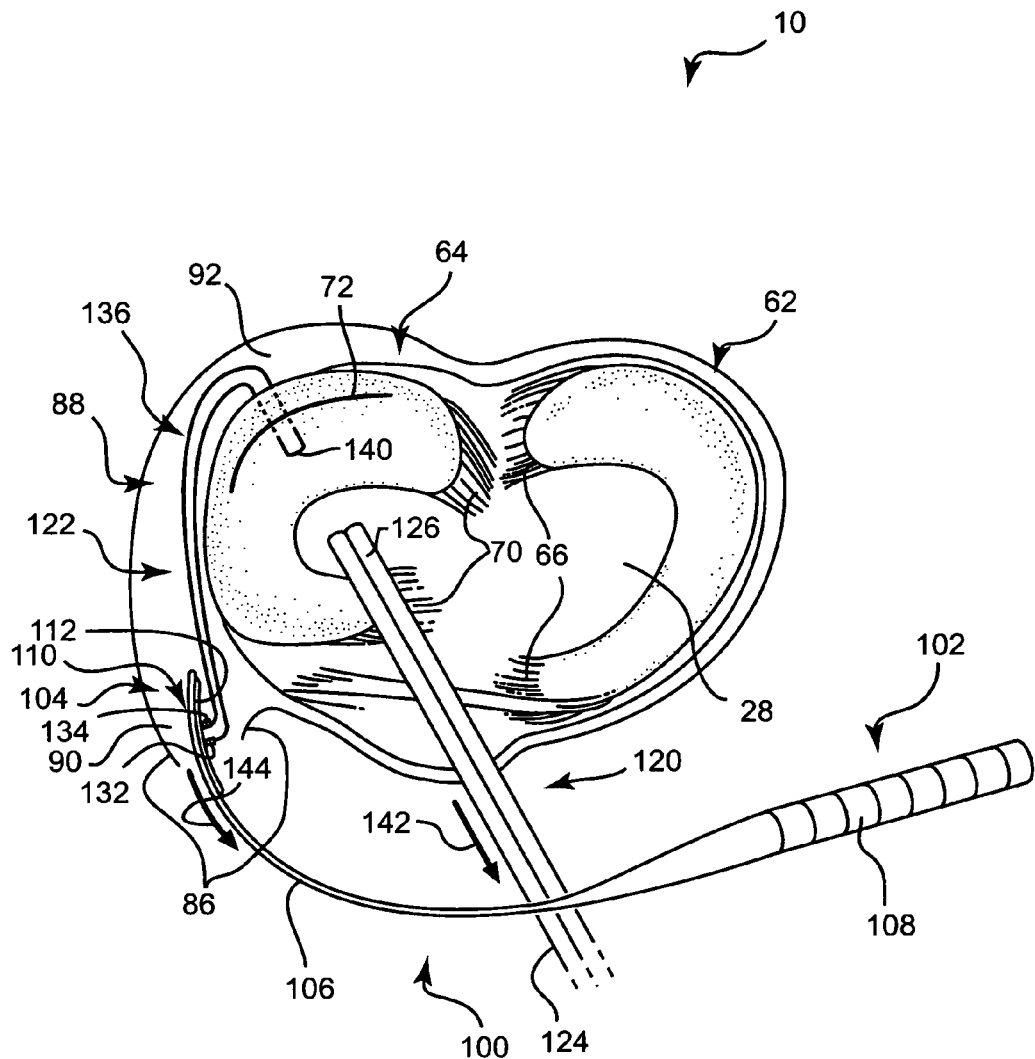
FIG. 5 is a cephalad section view of the knee, showing the central portion of the suture redundantly extending across the mensical tear, with the delivery instrument partially retracted from the meniscal tunnel and the implant delivery instrument partially retracted from the interior of the knee.

Referring to FIG. 5, a cephalad section view of the knee 10 illustrates the repair member 122 passing through the lateral meniscus 64, but not yet fully secured thereto. The instrument 100 has been partially retracted from the LMCT 88, and the delivery instrument 120 has been partially retracted from the interior of the knee 10. A central portion 140 of the repair member 122 is in the process of being drawn taught against the proximal surface of the lateral meniscus 64. The delivery instrument 120 will continue to be retracted through the interior space of the knee 10 along the direction shown by the arrow 142, and the instrument 100 will be retracted through the LMCT 88 along the direction shown by the arrow 144.

Since the barbs 138 of the repair member 122 are embedded in the pad 112, withdrawal of the distal end 104 through the LMCT 88 draws the ends 132, 134 of the repair member 122 through the LMCT 88. Once the distal end 104 has been withdrawn through the anterior portion 90 of the LMCT 88, the ends 132, 134 are outside the knee 10, and are therefore easily accessed by a surgeon.

Figure 6:
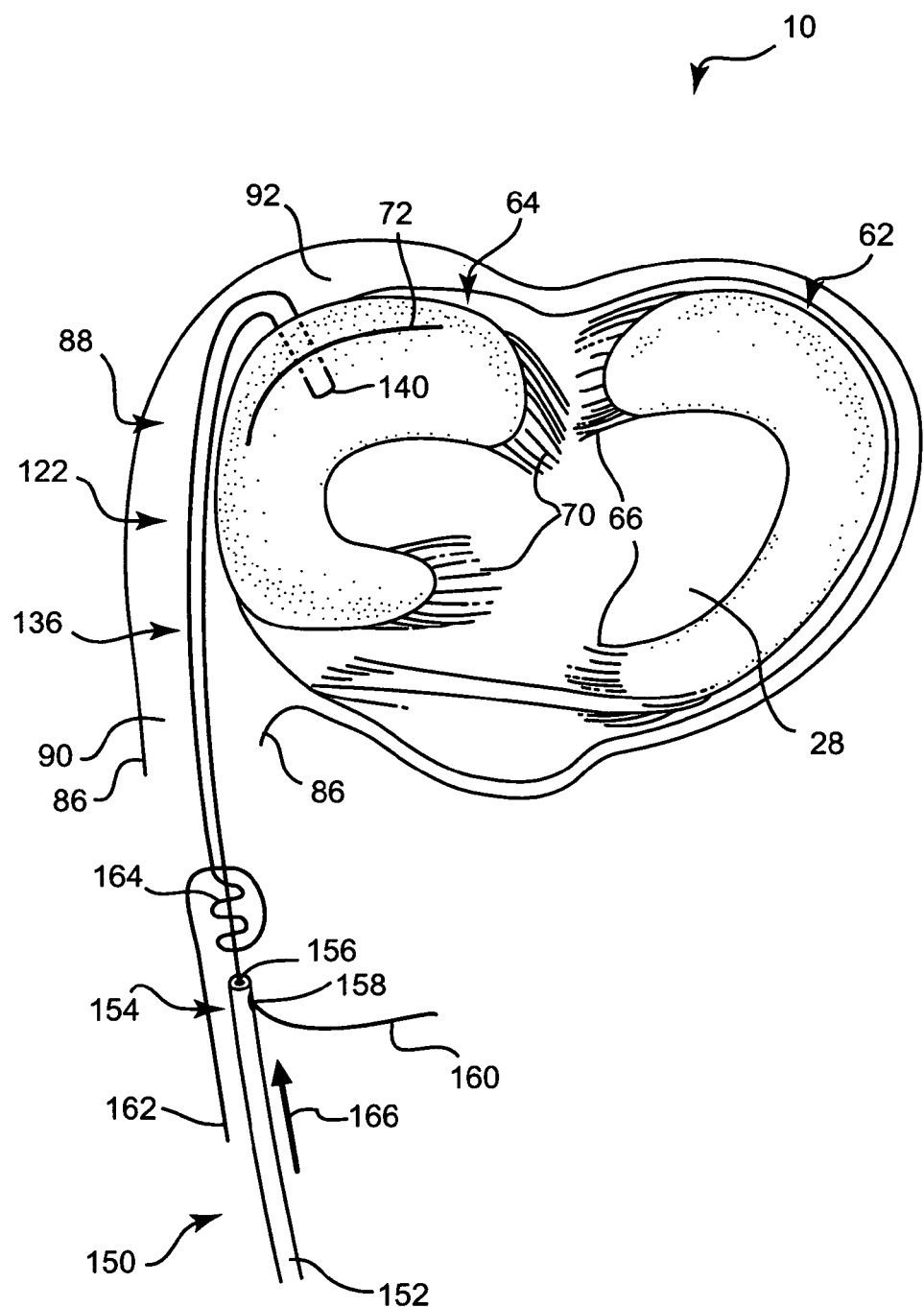
FIG. 6 is a cephalad section view of the knee, showing a sliding knot formed in the ends of the suture, and a knot pusher engaging one of the ends to push the knot toward the meniscal tear.

Referring to FIG. 6, a cephalad section view of the knee 10 illustrates the repair member 122 with the ends 132, 134 withdrawn from the LMCT 88. The suture 136 may advantageously be tied in place. However, it is much easier to form a knot in exposed suture ends than to do so within the confines of the posterior portion 92 of the LMCT 88. Accordingly, a push rod 150 may be employed.

As shown, the push rod 150 has a proximal end 152 and a distal end 154. The proximal end 152 is designed to be held by a surgeon, while the distal end 154 is shaped to retain two suture ends in such a manner that a knot can be pushed through a relatively narrow space, such as the LMCT 88, to tighten the suture. Thus, the distal end 154 may have a terminal aperture 156 and a peripheral aperture 158 that cooperate to receive an end of the suture 136 such that the end can be held relatively stationary to permit advancement of the distal end 154 along the suture.

The suture 136 may be cropped to remove the ends 132, 134, thereby removing the barbs 138 to detach the suture 136 from the pad 112. As a result, the suture 136 may have a first end 160 and a second end 162 that are not encumbered by barbs. The ends 160, 162 are tied in a knot 164, which may be of any configuration known to be appropriate for surgical use. In FIG. 6, the first end 160 passes through the terminal aperture 156 to enter the distal end 154, and then exits the distal end 154 through the peripheral aperture 158. The knot 164 may be formed by looping the second end 162 around the first end 160 in a desired pattern.

By advancing the distal end 154 along the first end 160 in the direction indicated by the arrow 166, the knot 164 may also be advanced along the first end 160 until it has passed through the anterior portion 90 of the LMCT 88 to reach the posterior portion 92. The knot 164 may be snugged against the interior wall of the LMCT 88 such that the tension within the central portion 140 of the suture 136 is sufficient to hold the tear 72 closed and to keep the knot 164 from loosening. The excess suture 136 of the first and second ends 160, 162 may then be cut away.

Figure 7:
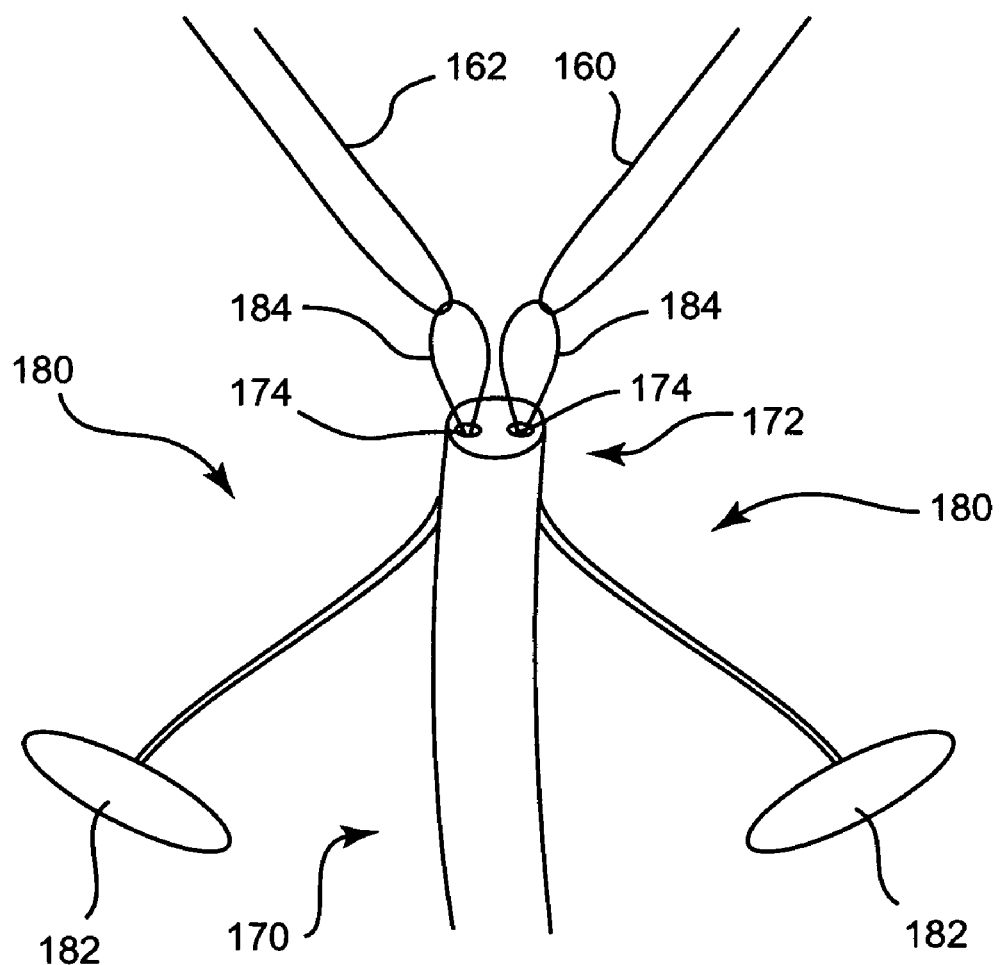
FIG. 7 is a cephalad section view of the knee, showing a suture passing system for passing the suture ends through a knot pusher configured differently from that of FIG. 6.

Referring to FIG. 7, a cephalad section view of the knee 10 illustrates push rod 170 of a suture passing system according to one alternative embodiment from that of FIG. 6. The push rod 170 has proximal end, which may be like the proximal end 152 of the push rod 150 of FIG. 6, and a distal end 172. The distal end 172 has two terminal apertures 174 and two peripheral apertures (not visible). Each terminal aperture 174 permits entry of one of the suture ends 160, 162 into the distal end 172, and the corresponding peripheral aperture permits egress of the suture end 160 or 162 from the distal end 172.

Thus, both suture ends 160, 162 may be held stationary while the distal end 172 is advanced to move a knot such as the knot 164 of FIG. 6 along both ends 160, 162, simultaneously. Motion of the knot 164 along both ends may advantageously avoid damage to the meniscal tissue proximate the tear 72 by avoiding the need to slide the suture 136 through the lateral meniscus 64. Otherwise, tension on the suture 136 perpendicular to its passage through the lateral meniscus 64 may cause the suture 136 to bite through the tissue of the meniscus 64.

As shown, threaders 180 may optionally be used to draw the ends 160, 162 through the terminal apertures 174 and through the corresponding peripheral apertures. Each of the threaders 180 may have a grip 182 such as a plastic post that is easily grasped by hand, and a loop 184 sized to easily receive one of the ends 160, 162. Each of the threaders 180 initially passes through one terminal aperture 174 and through the corresponding peripheral aperture, with the loop 184 protruding from the terminal aperture 174 as shown. Thus, a surgeon may easily insert the ends 160, 162 into the loops 184 and then draw the grips 182 to draw the loops 184, and therefore, the ends 160, 162, through the terminal apertures 174 and the peripheral apertures. The threaders 180 keep the surgeon from having to align the ends 160, 162 with the terminal apertures 174, which can be somewhat small.

In the alternative to usage of the instrument 100 and the push rod 150 or the push rod 170, the knot 164 may be tied within the posterior portion 92 of the LMCT 88. For example, a system of hooks, clippers, and/or other user-actuated devices (not shown) may be inserted into the LMCT 88 through a flexible cannula or the like, and used to cut away the first and second ends 132, 134 and to grasp and tie the ends 160, 162 together through the aid of an arthroscope. Alternatively, a threading device such as that of U.S. Pat. No. 6,171,317, may be inserted on the distal end of an instrument, and used to capture and tie the ends 160, 162 after removal of the barbs 138.

Figure 8A:
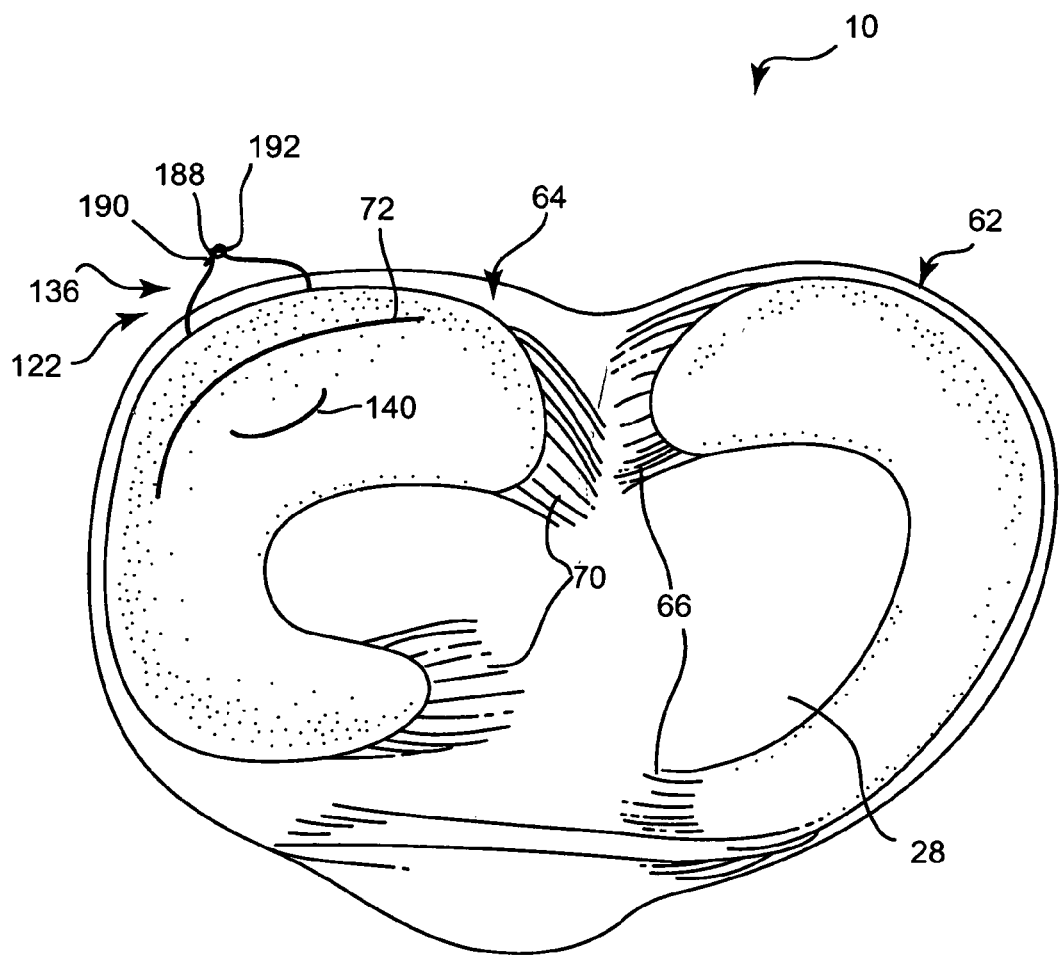
FIG. 8A is a cephalad section view of the knee, showing the suture in position to hold the meniscal tear closed via a knot positioned in the meniscal capsular tunnel, wherein the central portion of the suture redundantly bridges the meniscal tear.

Referring to FIG. 8A, a cephalad section view of the knee 10 illustrates the suture 136 in position to hold the tear 72 closed via the knot 164, which has been tightened to provide a tightened knot 188. The tissue or tissues that define the exterior wall of the LMCT 88 are not shown in FIG. 8A for simplicity. Although the suture 136 is shown somewhat loose for clarity, the knot 164 is tightened against the interior wall of the LMCT 88, as described previously so that the tension in the suture 136 maintains the knot 164 and holds the tear 72 closed. The central portion 140 of the suture 136 passes through the tear 72 twice. The first and second ends 160, 162 have been cut off adjacent to the tightened knot 188, leaving a first shortened end 190 and a second shortened end 192.

Figure 8B:
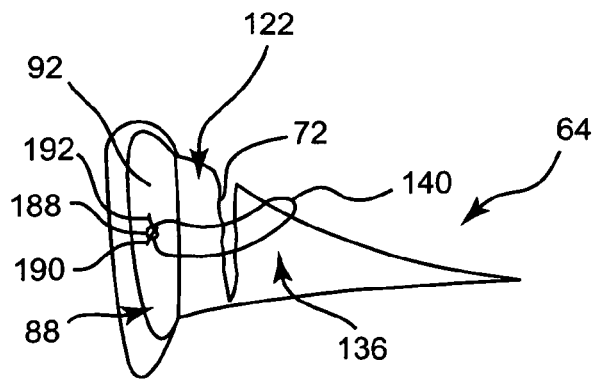
FIG. 8B is a lateral section view of the meniscus and suture of FIG. 8A.

Referring to FIG. 8B, a lateral section view illustrates the lateral meniscus 64 and the suture 136 of FIG. 8A. The LMCT 88 is again illustrated, and the section view is taken through the posterior portion 92 of the LMCT 88. The illustration of the tissues surrounding the LMCT 88 is not intended to be anatomically accurate; the description of FIGS. 1 and 2 provides greater detail regarding the location of the LMCT and the surrounding tissues. Again, although the suture 136 is shown somewhat loose in FIG. 8B for clarity, in operation, it is relatively tight.

Figure 9A:
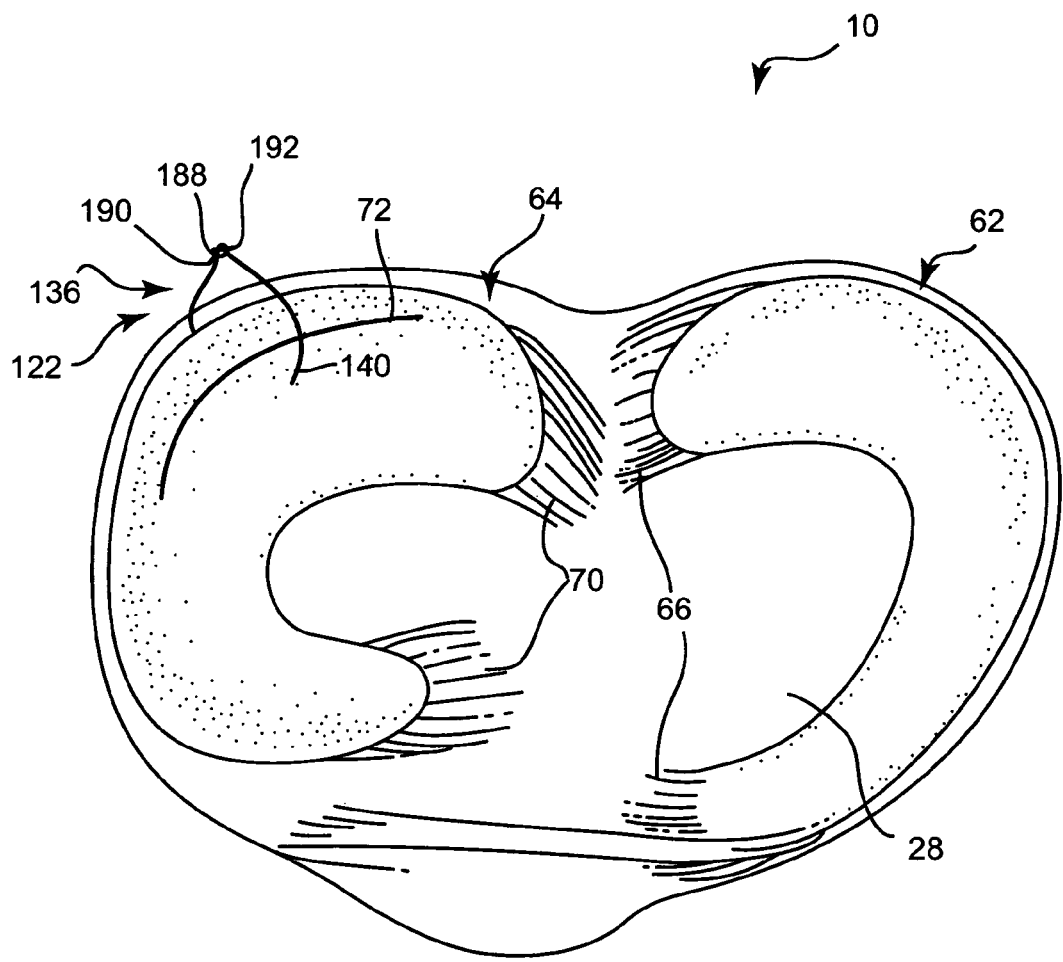
FIG. 9A is a cephalad section view of the knee, showing a suture in position to hold the meniscal tear closed via a knot positioned in the meniscal capsular tunnel, wherein part of the central portion of the suture bridges the tear, and the remainder of the central portion circumnavigates the tear proximally of the meniscus.

Referring to FIG. 9A, a cephalad section view of the knee 10 illustrates the suture 136 implanted in the lateral meniscus 64 in a different configuration. More precisely, in FIG. 9A, part of the central portion 140 of the suture 136 passes through the tear 72, while the remainder of the central portion 140 extends around the tear 72. As in FIGS. 8A and 8B, the suture 136 is tensioned to maintain the tightened knot 188 and to keep the tear 72 closed. The suture 136 thus operates in a manner similar to that of FIGS. 8A and 8B.

Procedures similar to those of FIGS. 3 through 6 may be employed to provide the suture configuration of FIG. 9A, with the exception that one of the ends 132 or 134 of the repair member 122 is not inserted through the lateral meniscus 64, but is instead passed proximally of the lateral meniscus 64, through the interior wall of the LMCT 88, and into the pad 112 or positioned to engage the instrument 100 in such a way as to facilitate repair of the tear 72.

Figure 9B:
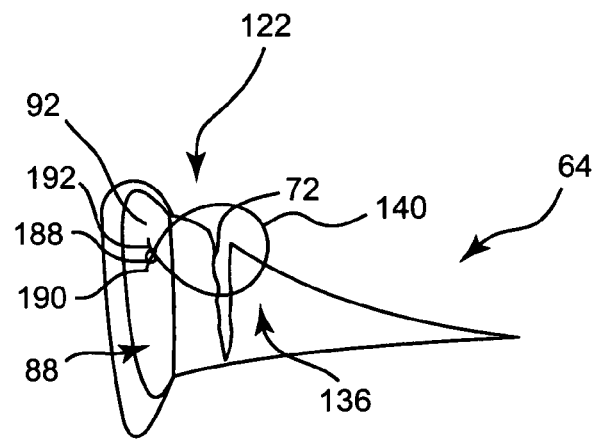
FIG. 9B is a lateral section view of the meniscus and suture of FIG. 9A.

Referring to FIG. 9B, a lateral section view illustrates the lateral meniscus 64 and the suture 136 in the arrangement of FIG. 9A. The suture 136 holds the tear 72 closed to promote healing in a manner similar to that of FIGS. 8A and 8B.

Figure 10A:
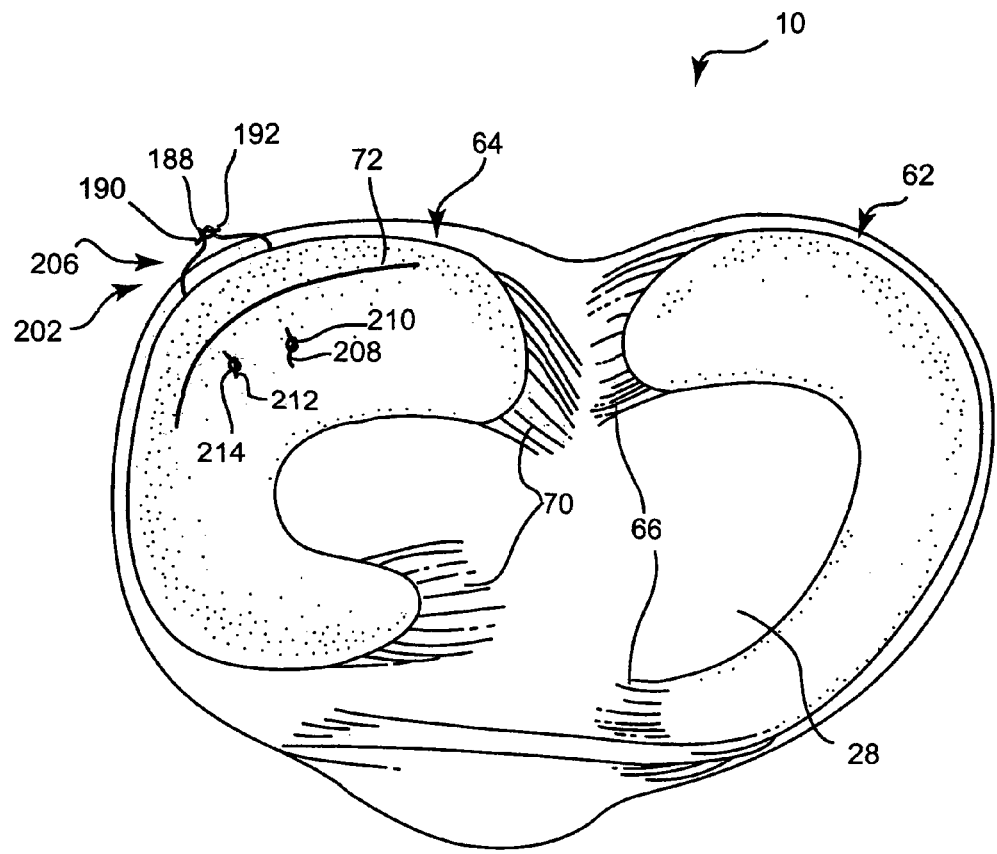
FIG. 10A is a cephalad section view of the knee, showing a repair member in the form of two strands of suture terminated with a knot on each end with a knot secured in the meniscal capsular tunnel to tie the strands together.

Referring to FIG. 10A, a cephalad section view of the knee 10 illustrates the use of a repair member 202 according to one alternative embodiment of the invention. As shown, the repair member 202 includes a suture 206 divided into two strands. One strand has a first proximal end 208 secured to the proximal surface of the lateral meniscus 64 by a first proximal knot 210. The other strand has a second proximal end 212 secured to the proximal surface of the lateral meniscus 64 by a second proximal knot 214. The proximal ends 208, 212 are unable to slide into the tissue of the meniscus 64 due to the presence of the proximal knots 210, 214. The opposite ends of the strands are tied together in a knot, which may be identical to the tightened knot 188 of FIGS. 8A through 9B.

The repair member 202 may be implanted in a manner similar to that set forth in the description of FIGS. 3 through 6. Accordingly, one end of each of the strands of the suture 206 may initially be coupled to a barb, and the other end may initially be knotted with either the first proximal knot 210 or the second proximal knot 214. A delivery instrument such as the delivery instrument 120 of FIGS. 4A and 5 may be used to insert the strands through the lateral meniscus 64 such that the barbs are embedded in the pad 112 of an instrument such as the instrument 100. The ends 132, 134 of the strands are removed from the LMCT 88 via the instrument, the ends 132, 134 are cut off to provide the ends 160, 162 without barbs, and a knot is pushed along the ends 160, 162 to provide the tightened knot 188. Usage of a push rod such as the push rod 170 of FIG. 170 may be necessary, since neither strand of the suture 206 can slide through the tissue of the lateral meniscus 64.

Figure 10B:
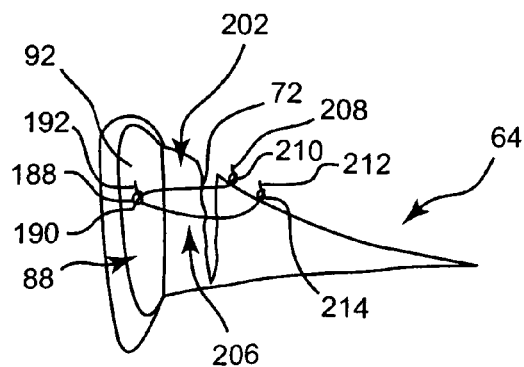
FIG. 10B is a lateral section view of the meniscus and suture strands of FIG. 10A.

Referring to FIG. 10B, a lateral section view illustrates the lateral meniscus 64 and the repair member 202 of FIG. 10A. Both strands of the suture 206 pass through the tear 72. The tightened knot 188 maintains tension in the strands to maintain the tightened knot 188 and keep the tear 72 closed.

Figure 11A:
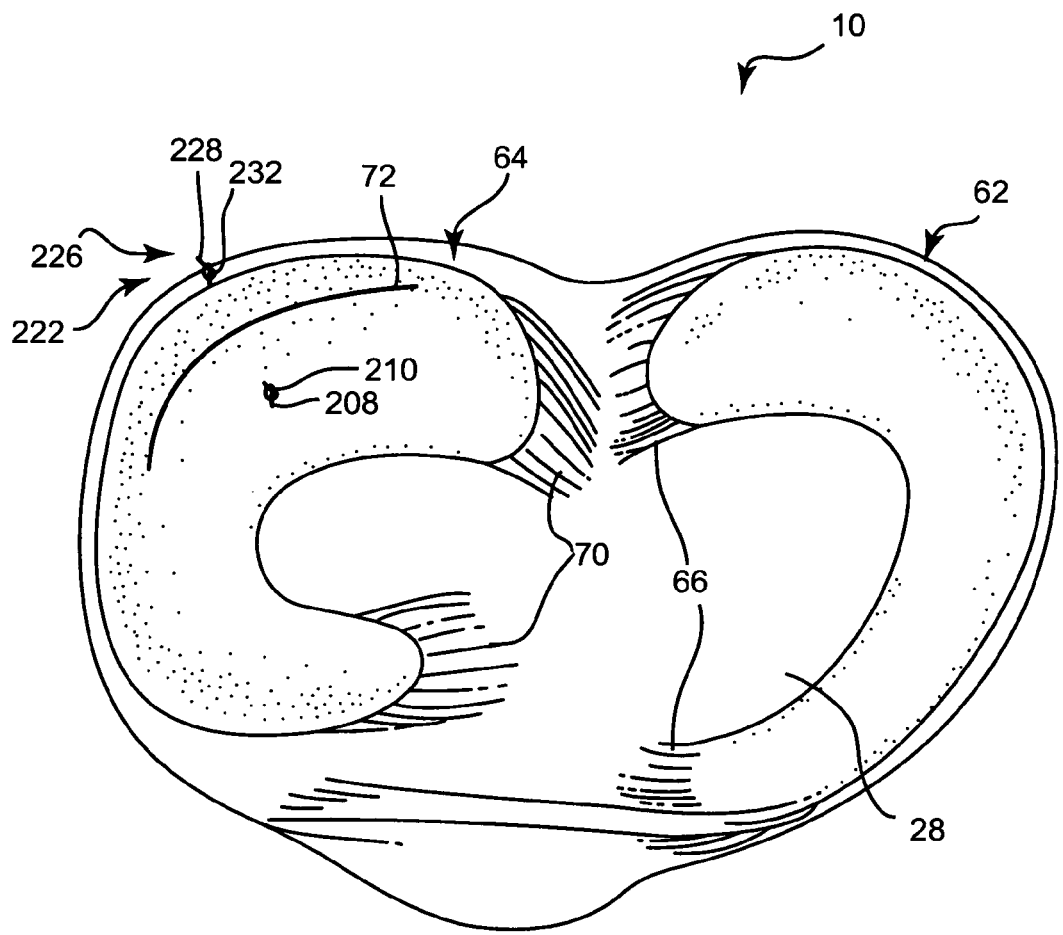
FIG. 11A is cephalad section view of the knee, showing a repair member in the form of one strand of suture terminated with a knot both ends, with one of the knots secured in the meniscal capsular tunnel.

Referring to FIG. 11A, cephalad section view of the knee 10 illustrates a repair member 242 according to another alternative embodiment of the invention. As shown, the repair member 242 has a suture 246 with only a single strand. The suture 246 has a first proximal end 208 and a first proximal knot 210 near the first proximal end 208 to keep the first proximal end from sliding into the tissue of the lateral meniscus 64. The suture 246 also has a distal end 228 with a distal knot 232 formed therein to keep the distal end 228 from sliding into the tissue of the lateral meniscus 64.

The repair member 242 may be implanted in a manner somewhat similar to the procedures set forth previously. More precisely, a delivery instrument having single lumen may be used to insert the distal end 228, with an attached barb (not shown), through the lateral meniscus 64, through the interior wall of the LMCT 88, and into a pad 112 of an instrument such as the instrument 100. The first proximal knot 210 is provided prior to insertion of the suture 246 into the knee 10. The distal end 228 is withdrawn through the LMCT 88 and a method such as that of FIG. 6 is used to push the knot back along the distal end 228 to provide the distal knot 232. Since the knot must be formed in the distal end 228 and pushed along the distal end 228, a knot configuration different from that of the knot 164 may be needed.

Figure 11B:
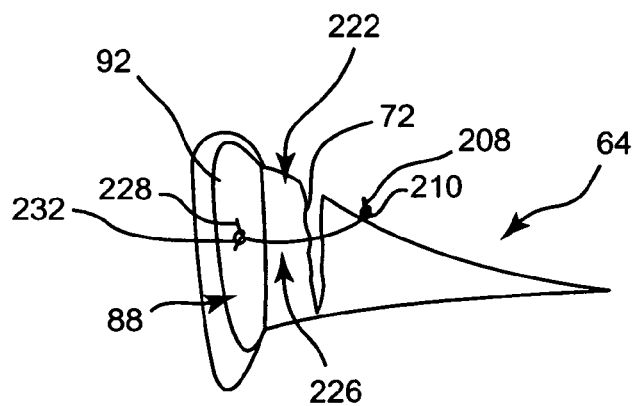
FIG. 11B is a lateral section view of the meniscus and suture strand of FIG. 11A.

Referring to FIG. 11B, a lateral section view illustrates the lateral meniscus 64 and the repair member 242 of FIG. 11A. As shown, the suture 246 passes through the tear 72. The distal knot 232 is pushed against the interior wall of the LMCT 88 to provide tension in the suture 246 to keep the distal knot 232 tight and to close the tear 72.

Figure 12A:
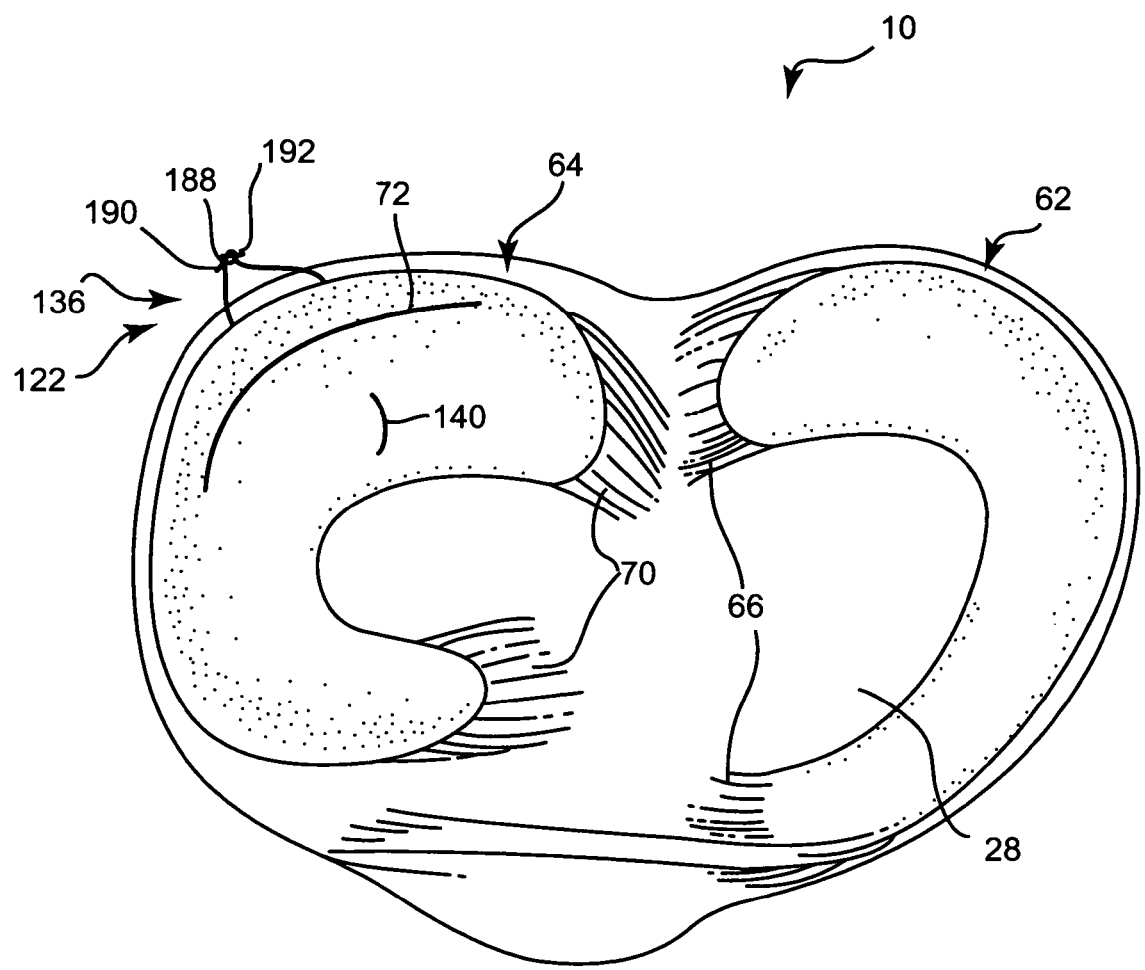
FIG. 12A is a cephalad section view of the knee, showing a repair member in the form of a suture in position to hold the meniscal tear closed via a knot positioned in the meniscal capsular tunnel, wherein part of the central portion of the suture bridges the tear, and the remainder of the central portion circumnavigates the tear distally of the meniscus.

Referring to FIG. 12A, a cephalad section view of the knee 10 illustrates the repair member 122 applied to provide another alternative configuration from that of FIGS. 8A and 8B. The central portion 140 of the suture 136 of the repair member 122 is arranged such that part of the central portion 140 passes through the tear 72 of the lateral meniscus 64, while the remainder extends around the tear 72, along the distal surface of the meniscus 64.

Procedures similar to those of FIGS. 3 through 6 may be employed to provide the suture configuration of FIG. 12A, with the exception that one of the ends 132 or 134 of the repair member 122 is not inserted through the lateral meniscus 64, but is instead passed distally of the lateral meniscus 64, through the interior wall of the LMCT 88, and into the pad 112.

Figure 12B:
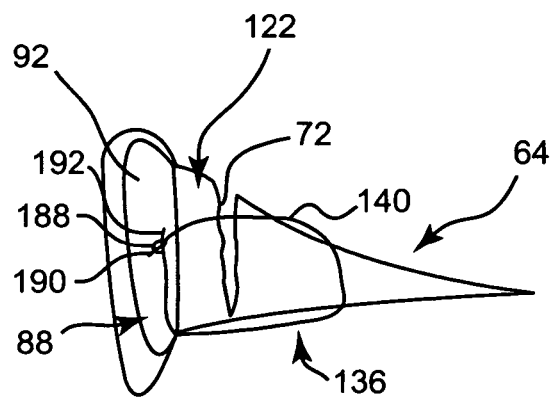
FIG. 12B is a lateral section view of the meniscus and suture of FIG. 12A.

Referring to FIG. 12B, a lateral section view illustrates the lateral meniscus 64 and the suture 136 in the arrangement of FIG. 12A. The suture 136 holds the tear 72 closed to promote healing in a manner similar to that of FIGS. 8A and 8B.

Figure 13A:
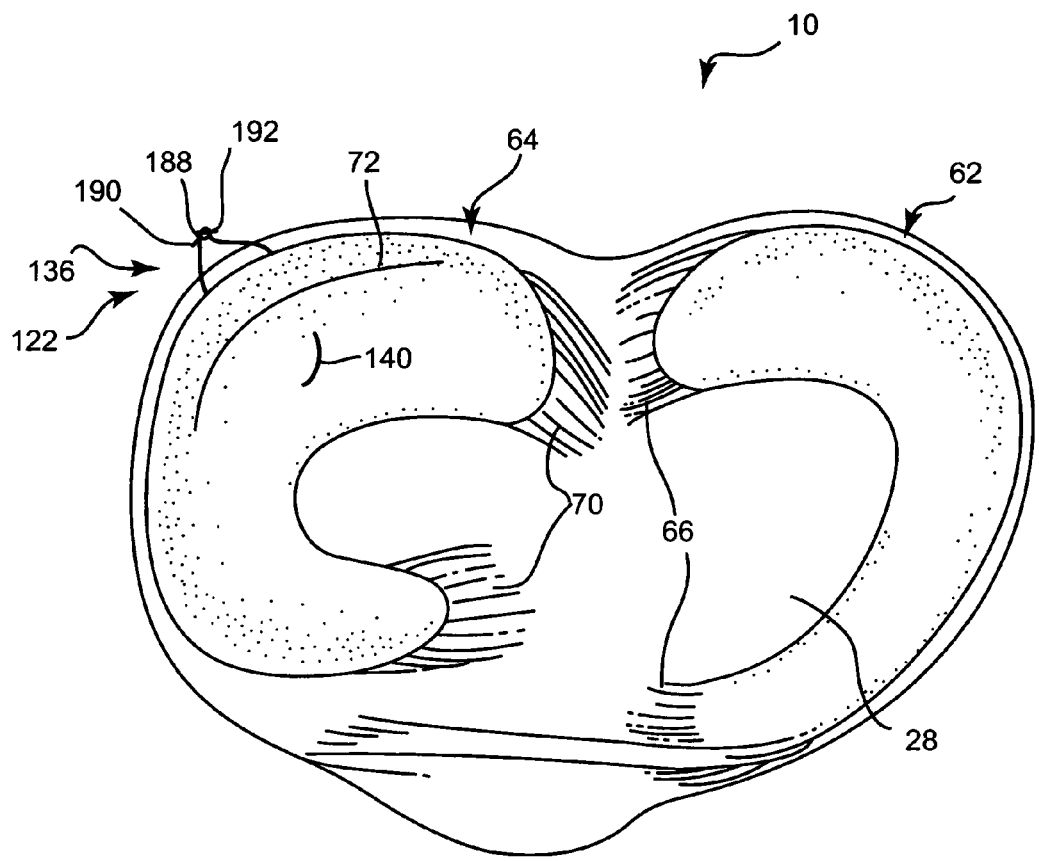
FIG. 13A is a cephalad section view of the knee, showing a repair member in the form of a suture in position to hold the meniscal tear closed via a knot positioned in the meniscal capsular tunnel, wherein the central portion of the suture redundantly bridges the meniscal tear, and the central portion extends generally radially along the proximal surface of the meniscus.

Referring to FIG. 13A, a cephalad section view of the knee 10 illustrates the repair member 122 applied to provide another alternative configuration from that of FIGS. 8A and 8B. As in FIGS. 8A and 8B, the central portion 140 of the suture 136 of the repair member 122 is arranged such that the central portion 140 redundantly passes through the tear 72. In FIGS. 8A and 8B, the part of the central portion 140 left exposed on the proximal side of the lateral meniscus 64 extends generally parallel to the circumferential tissue fibers of the lateral meniscus 64. In FIG. 13A, the part of the central portion 104 left exposed on the proximal side extends generally radially to cross the circumferential tissue fibers of the lateral meniscus 64.

Accordingly, the loop formed by the suture 136 in FIG. 13A captures the circumferential tissue fibers, which are generally known to be relatively strong. Thus, the configuration of FIG. 13A may provide relatively more secure anchoring of the suture 136 to prevent the suture 136 from loosening or pulling through the tissue of the meniscus 64 in response to the tension applied.

Procedures similar to those of FIGS. 3 through 6 may be employed to provide the suture configuration of FIG. 13A, with the exception that, rather than orienting the delivery instrument 120 such that the two lumens are offset from each other along the medial and lateral directions 20, 22, as in FIG. 4, the delivery instrument 120 may be oriented such that the lumens are offset from each other along the cephalad and caudal directions 12, 14. The cephalad/caudal offset enables the suture 136 to capture the circumferential tissue fibers.

Figure 13B:
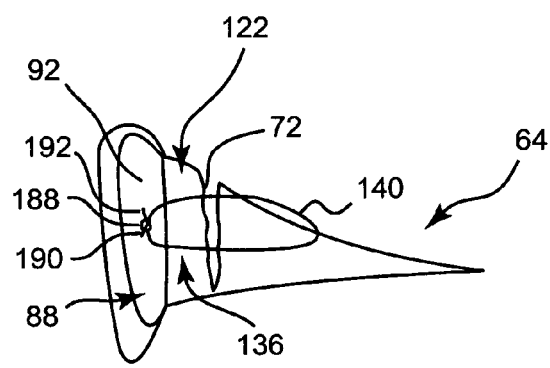
FIG. 13B is a lateral section view of the meniscus and suture of FIG. 13A.

Referring to FIG. 13B, a lateral section view illustrates the lateral meniscus 64 and the suture 136 in the arrangement of FIG. 13A. The suture 136 holds the tear 72 closed to promote healing in a manner similar to that of FIGS. 8A and 8B, while capturing the circumferential tissue fibers to enhance retention.

Figure 14A:
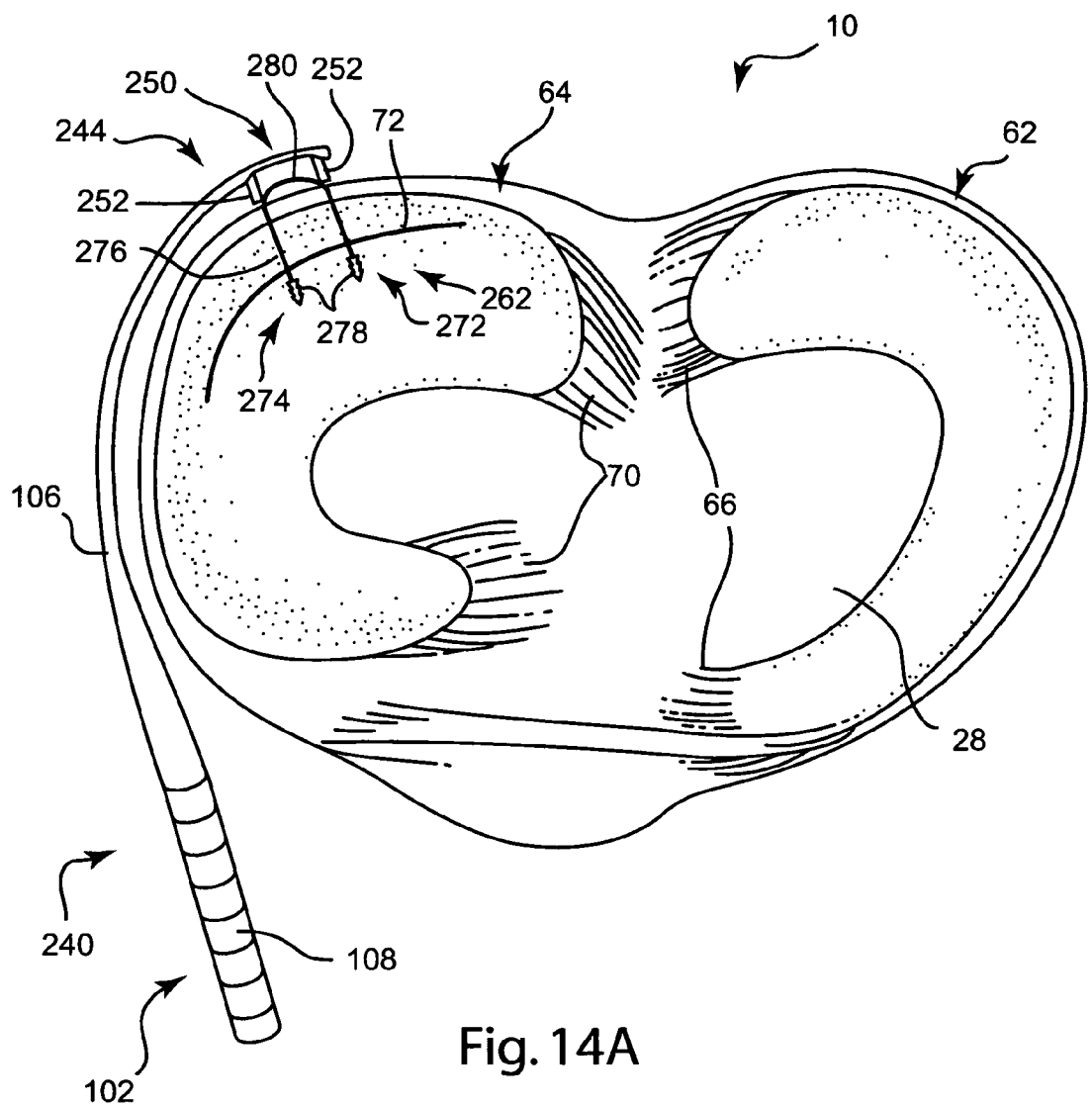
FIG. 14A is a cephalad section view of the knee, showing a repair member in the form of a suture with two barbed ends, each of which is inserted into the meniscus from the meniscal capsular tunnel to bridge the tear.

Referring to FIG. 14A, a cephalad section view of the knee 10 illustrates a repair system according to another alternative embodiment of the invention. As shown, a delivery and securement instrument 240, or instrument 240, may have a proximal end 102, a distal end 244, and an intermediate portion 106 that spans the displacement between the proximal and distal ends 102, 244. The proximal end 102 has a handle 108 shaped to be grasped by a surgeon, and the distal end 244 has a delivery interface 250 having a pair of suture end retainers 252 protruding along a direction generally perpendicular to the remainder of the instrument 240.

The instrument 240 is designed to insert a repair member 262 into the lateral meniscus 64. The repair member 262 may have a first end 272 and a second end 274 designed to be driven into the tissue of the lateral meniscus 64 by the delivery interface 250. The repair member 262 includes a length of suture 276 and a pair of barbs 278 secured to the ends of the length of suture 276 to form the ends 272, 274. The repair member 262 also has a central portion 280 that extends between the first and second ends 272, 274.

The suture end retainers 252 may comprise posts with recesses or other structures that retain the barbs 278 to keep the barbs 278 protruding outward until the barbs 278 are implanted into the tissue of the lateral meniscus 64. In operation, the repair member 262 may be secured to the delivery interface 250, and the distal end 244 of the instrument 240 may be inserted into and through the LMCT 88 in a manner similar to that of the distal end 104 of the instrument 100. When the distal end 244 and the repair member 262 are positioned posteriorly of the tear 72, the distal end 244 may be urged anteriorly to insert the barbs 278 into the tissue of the lateral meniscus 64 until the barbs 278 have passed through the tear 72 and the central portion 280 is pressed relatively tightly against the interior surface of the LMCT 88.

The repair member 262 need not be secured to the lateral meniscus 64 independently of insertion of the repair member 262 into the lateral meniscus 64 because, upon full insertion of the repair member 262, the barbs 278 keep the repair member 262 in place without requiring the performance of additional steps. The barbs 278 remain in the lateral meniscus 64, and are thus biocompatible, and may also be bioabsorbable, if desired. After the repair member 262 has been inserted and secured, the instrument 240 may be withdrawn from the LMCT 88.

Figure 14B:
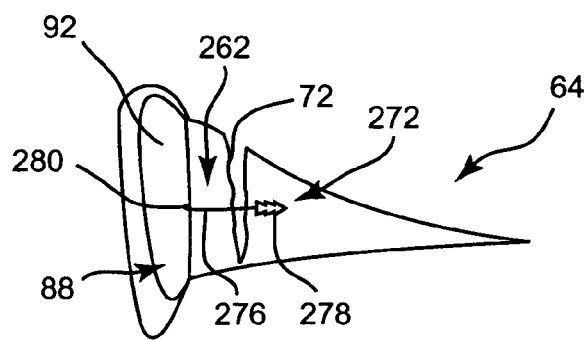
FIG. 14B is a lateral section view of the meniscus and suture of FIG. 14A.

Referring to FIG. 14B, a lateral section view illustrates the lateral meniscus 64 and the repair member 262 of FIG. 14A. The central portion 280 of the repair member 262 passes redundantly through the tear 72, and the tension in the repair member 262 keeps the barbs 278 securely seated in place, and keeps the tear 72 closed to permit healing.

Figure 15A:
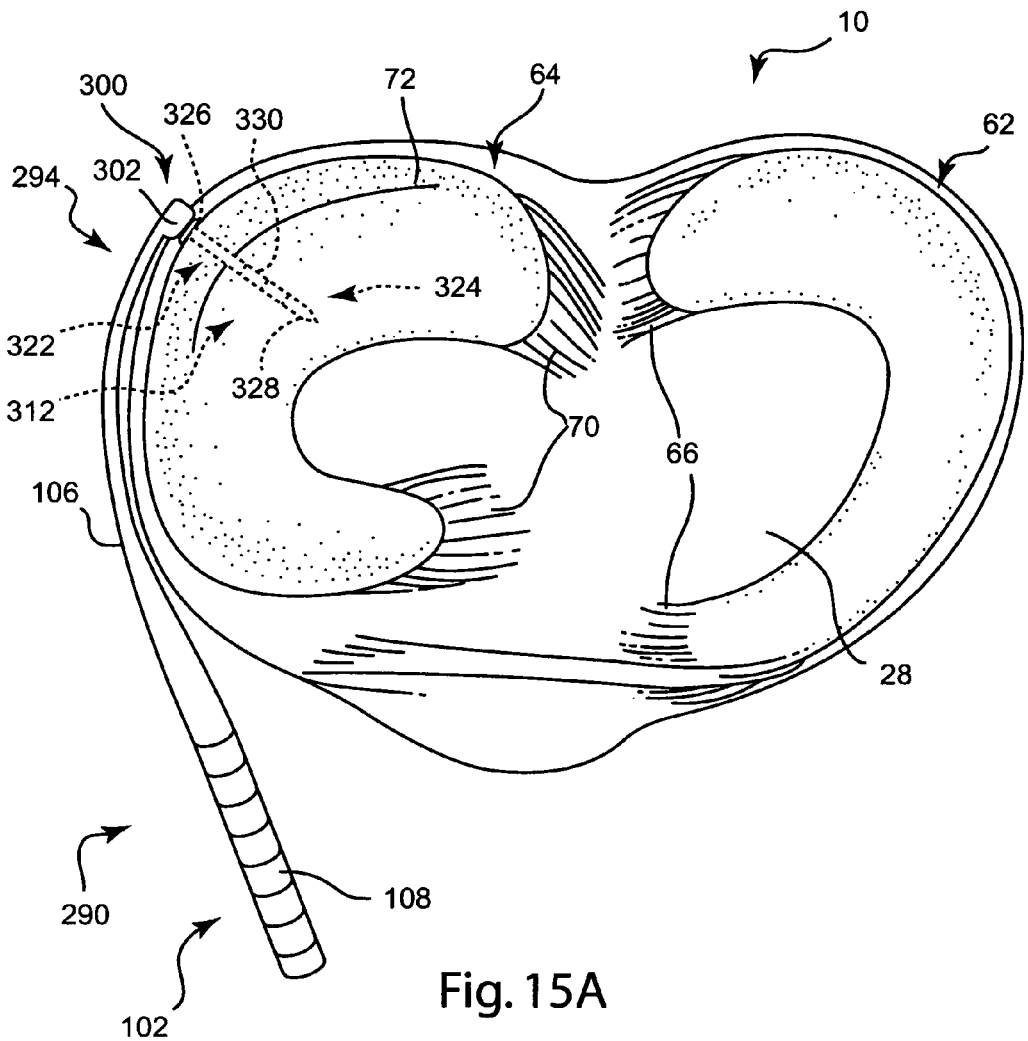
FIG. 15A is a cephalad section view of the knee, showing a repair member in the form of a barbed post bridging the meniscal tear with barbs imbedded in the meniscal tissue, and a head in the meniscal capsular tunnel.

Referring to FIG. 15A, a cephalad section view of the knee 10 illustrates a repair system according to another alternative embodiment of the invention. The repair system includes a delivery and securement instrument 290, or instrument 290. The instrument 290 has a proximal end 102, a distal end 294, and an intermediate portion 106 that spans the distance between the proximal end 102 and the distal end 294. The proximal end 102 has a handle 108 shaped be grasped by a surgeon, and the distal end 294 has a delivery interface 300 with a head retainer 302 that protrudes generally perpendicularly from the instrument 290.

The instrument 290 is designed to insert a repair member 312 into the lateral meniscus 64. The repair member 312 may have a first end 322 and a second end 324 designed to be driven into the tissue of the lateral meniscus 64 by the delivery interface 290. The first end 322 has a head 326, and the second end 324 has barbs 328 that facilitate one-way passage of the second end 324 through tissue and retention of the second end 324 in the tissue. A central portion 330 extends between the head 326 and the barbs 328. The barbs 328 may have a sawtooth shape on one side of the repair member 312, or may instead be circumferentially positioned around the central portion 330 of the repair member 312. Alternatively, the barbs 328 may have threaded, unitary, continuous or discontinuous helical protrusions circumferentially positioned around the central portion 330 of the repair member 312.

The head retainer 302 may comprise a recess or other structure that retains the head 326 to keep the barbs 328 protruding outward until the barbs 328 are implanted into the tissue of the lateral meniscus 64. In operation, the repair member 312 may be secured to the delivery interface 300, and the distal end 294 of the instrument 290 may be inserted into and through the LMCT 88 in a manner similar to that of the distal end 104 of the instrument 100. When the distal end 294 and the repair member 312 are positioned posteriorly of the tear 72, the distal end 294 may be urged anteriorly to insert the barbs 328 into the tissue of the lateral meniscus 64 until the barbs 328 have passed through the tear 72 and the head 326 is pressed relatively tightly against the interior surface of the LMCT 88.

As with the previous embodiment, the repair member 312 need not be secured to the lateral meniscus 64 independently of insertion of the repair member 312 into the lateral meniscus 64 because, upon full insertion of the repair member 312, the barbs 328 keep the repair member 312 in place without requiring the performance of additional steps. The barbs 328 remain in the lateral meniscus 64, and are thus biocompatible, and may also be bioabsorbable, if desired. After the repair member 312 has been inserted and secured, the instrument 290 may be withdrawn from the LMCT 88.

Figure 15B:
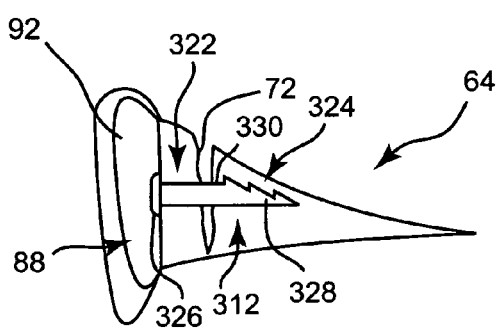
FIG. 15B is a lateral section view of the meniscus and post of FIG. 15A.

Referring to FIG. 15B, a lateral section view illustrates the lateral meniscus 64 and the repair member 312 of FIG. 15A. The central portion 330 of the repair member 262 passes through the tear 72, and the tension in the repair member 312 keeps the barbs 328 securely seated in place, and keeps the tear 72 closed to permit healing.

Figure 16A:
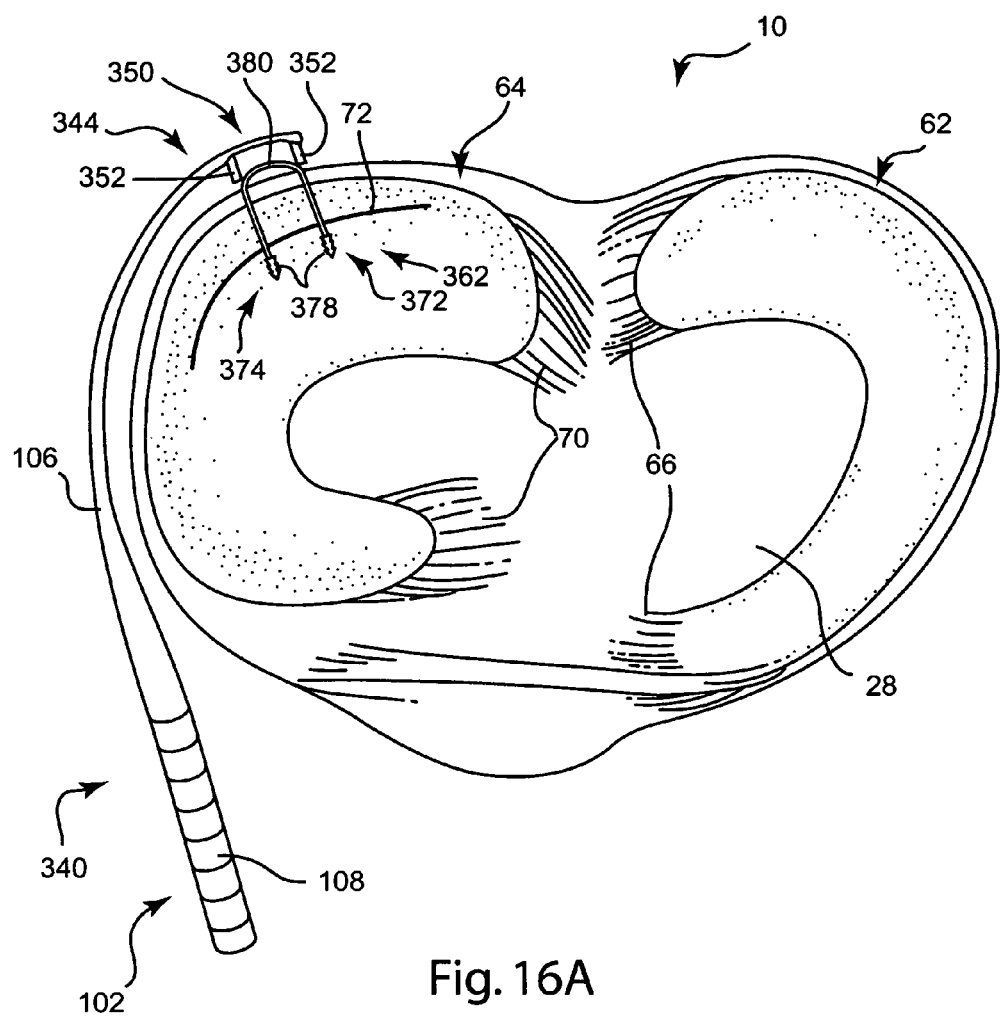
FIG. 16A is a cephalad section view of the knee, showing a repair member in the form of a staple with two barbed ends, each of which is inserted into the meniscus from the meniscal capsular tunnel to bridge the tear.

Referring to FIG. 16A, a cephalad section view of the knee 10 illustrates a repair system according to another alternative embodiment of the invention. As shown, a delivery and securement instrument 340, or instrument 340, may have a proximal end 102, a distal end 344, and an intermediate portion 106 that spans the displacement between the proximal and distal ends 102, 344. The proximal end 102 has a handle 108 shaped to be grasped by a surgeon, and the distal end 344 has a delivery interface 350 having a pair of staple retainers 352 protruding along a direction generally perpendicular to the remainder of the instrument 340.

The instrument 340 is designed to insert a repair member 362 into the lateral meniscus 64. The repair member 362 may have a first end 372 and a second end 374 designed to be driven into the tissue of the lateral meniscus 64 by the delivery interface 350. The repair member 362 includes a pair of barbs 378 positioned at the first and second ends 372, 374, and a central portion 380 that extends between the first and second ends 372, 374.

The staple retainers 352 may comprise posts with recesses or other structures that retain the central portion 380 and/or the barbs 378 to keep the barbs 378 protruding outward until the barbs 378 are implanted into the tissue of the lateral meniscus 64. In operation, the repair member 362 may be secured to the delivery interface 350, and the distal end 344 of the instrument 340 may be inserted into and through the LMCT 88 in a manner similar to that of the distal end 104 of the instrument 100. When the distal end 344 and the repair member 362 are positioned posteriorly of the tear 72, the distal end 344 may be urged anteriorly to insert the barbs 378 into the tissue of the lateral meniscus 64 until the barbs 378 have passed through the tear 72 and the central portion 380 is pressed relatively tightly against the interior surface of the LMCT 88.

As in the previous two embodiments, the repair member 362 need not be secured to the lateral meniscus 64 independently of insertion of the repair member 362 into the lateral meniscus 64 because, upon full insertion of the repair member 362, the barbs 378 keep the repair member 362 in place without requiring the performance of additional steps. The entire repair member 362 remains in the knee 10, and is therefore biocompatible, and may also be bioabsorbable, if desired. After the repair member 362 has been inserted and secured, the instrument 340 may be withdrawn from the LMCT 88.

Figure 16B:
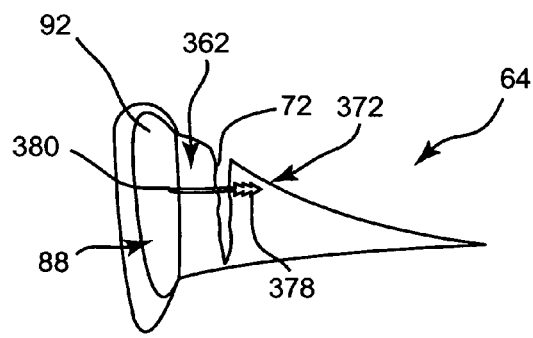
FIG. 16B is a lateral section view of the meniscus and staple of FIG. 16A.

Referring to FIG. 16B, a lateral section view illustrates the lateral meniscus 64 and the repair member 362 of FIG. 16A. The central portion 380 of the repair member 362 passes redundantly through the tear 72, and the tension in the repair member 362 keeps the barbs 378 securely seated in place, and keeps the tear 72 closed to permit healing.

Figure 17A:
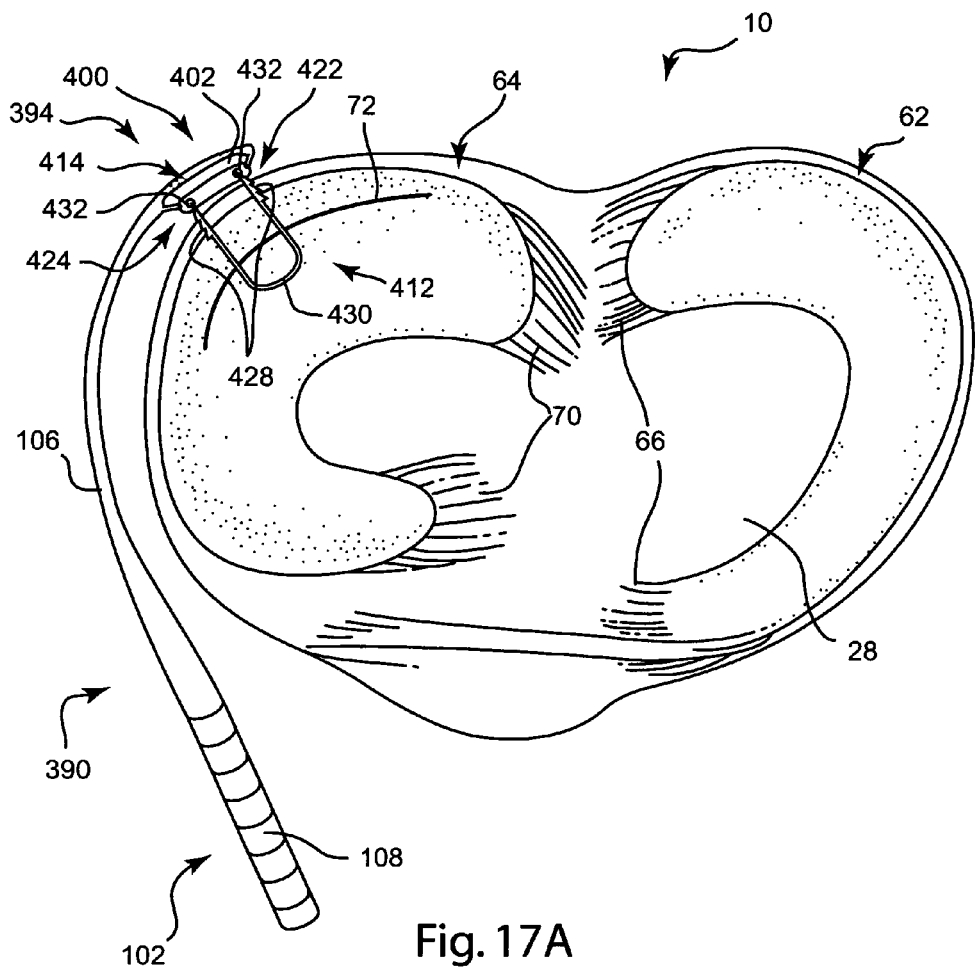
FIG. 17A is a cephalad section view of the knee, showing a repair member in the form of a two-piece implant with a staple with two barbed ends, each of which is inserted through the meniscal tear from the anterior side, and a retainer having two openings that receive and retain the barbed ends to secure them within the meniscal capsular tunnel.

Referring to FIG. 17A, a cephalad section view of the knee 10 illustrates a repair system according to another alternative embodiment of the invention. As shown, a securement instrument 390, or instrument 390, may have a proximal end 102, a distal end 394, and an intermediate portion 106 that spans the displacement between the proximal and distal ends 102, 394. The proximal end 102 has a handle 108 shaped to be grasped by a surgeon, and the distal end 394 has a retention interface 400 having a recess 402 with an elongated shape.

The instrument 390 is designed to secure a repair member 412 that has been inserted into the lateral meniscus 64 from a position anteriorly of the tear 72 by a method similar to that employed in FIGS. 4 and 5. The recess 402 is shaped to hold a coupling member 414 attachable to the repair member 412 to secure the repair member to the lateral meniscus 64.

The repair member 412 may have a first end 422 and a second end 424 designed to be driven into the tissue of the lateral meniscus 64 by a delivery instrument (not shown), which may be somewhat similar to the delivery instrument 120 of FIGS. 4 and 5. The repair member 412 includes a pair of barbs 428 positioned at the first and second ends 422, 424, and a central portion 430 that extends between the first and second ends 422, 424. The coupling member 414 has a pair of apertures 432 spaced apart such that the ends 422, 424 can be simultaneously inserted into the apertures 432. The apertures 432 are sized such that the barbs 428 are insertable through the apertures 432, but then cannot be withdrawn through the apertures 432.

In operation, the distal end 394 of the instrument 390 is first inserted through the LMCT 88 until the distal end 394 is positioned posteriorly of the tear 72. The repair member 412 is then inserted into the lateral meniscus 64 in such a manner that the ends 422, 424 pass through the tear 72, through the remainder of the lateral meniscus 64, and through the interior wall of the LMCT 88. As mentioned previously, a delivery instrument (not shown) similar to the delivery instrument 120 may be used to insert the repair member 412 into the lateral meniscus 64.

The apertures 432 may be aligned with the ends 422, 424 of the repair member 412, and the distal end 394 may be actuated anteriorly to insert the barbs 428 through the apertures 432. The coupling member 414 is then pressed relatively tightly against the interior surface of the LMCT 88. After the repair member 412 has been secured, the instrument 390 may be withdrawn from the LMCT 88. The repair member 412 and the coupling member 414 both remain in the knee 10; accordingly, both are biocompatible, and may also be bioabsorbable, if desired.

Figure 17B:
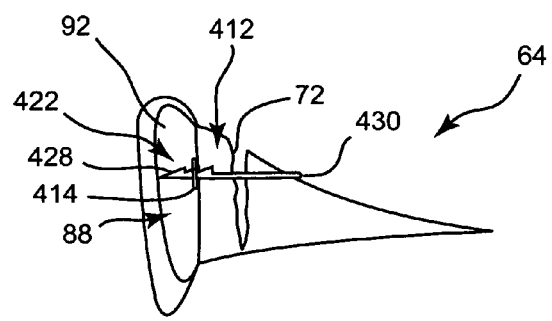
FIG. 17B is a lateral section view of the meniscus and the repair member of FIG. 17A.

Referring to FIG. 17B, a lateral section view illustrates the lateral meniscus 64, the repair member 412, and the coupling member 414 of FIG. 17A. The central portion 430 of the repair member 412 passes redundantly through the tear 72, and the tension in the repair member 412 keeps the barbs 428 securely seated in place, and keeps the tear 72 closed to permit healing.

Figure 18A:
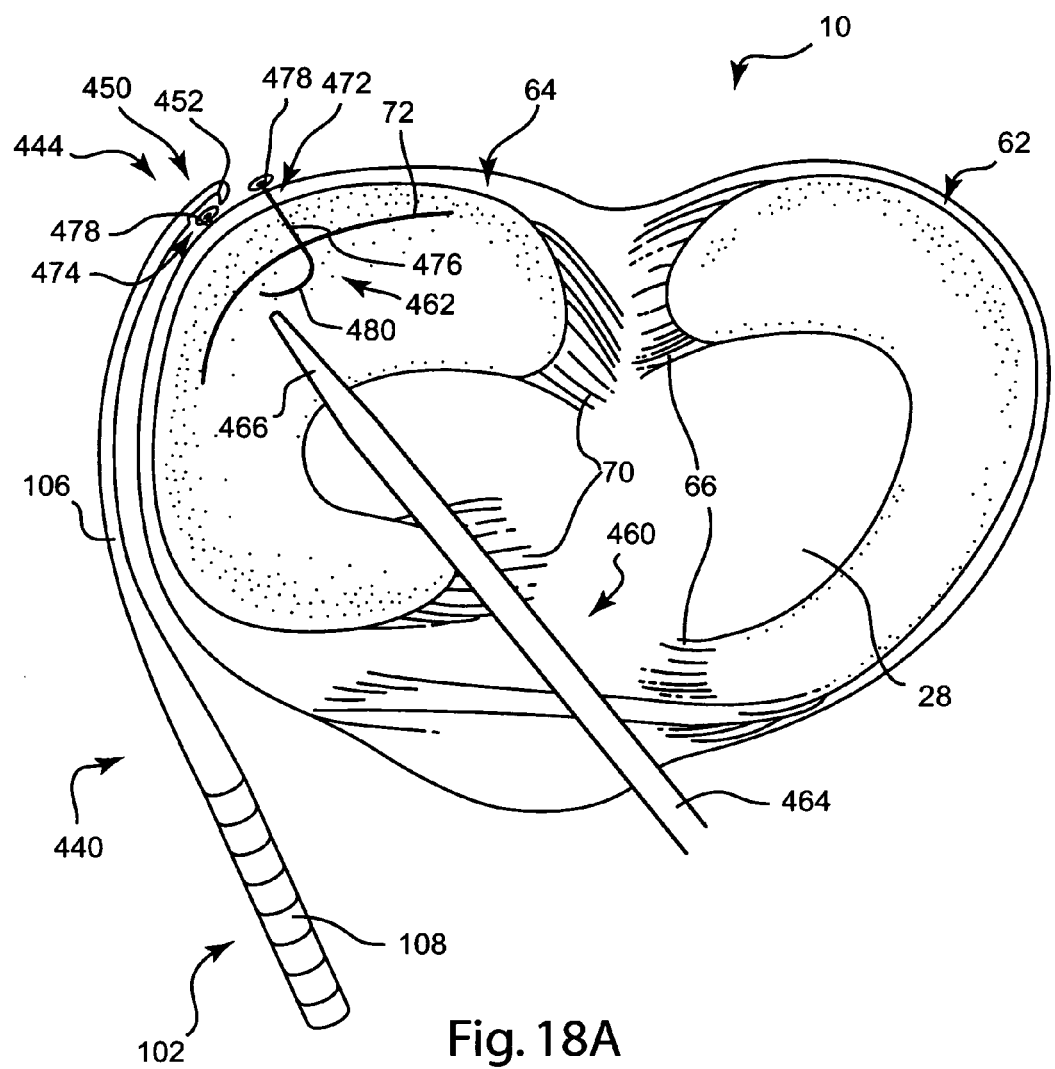
FIG. 18A is a cephalad section view of the knee, showing a repair member in the form of a length of suture with rotatable "flip" anchors at each end, with the ends inserted through the meniscal tear from the anterior side, and rotated within the meniscal capsular tunnel to retain the repair member.

Referring to FIG. 18A, a cephalad section view of the knee 10 illustrates a repair system according to another alternative embodiment of the invention. As shown, a securement instrument 440, or instrument 440, may have a proximal end 102, a distal end 444, and an intermediate portion 106 that spans the displacement between the proximal and distal ends 102, 444. The proximal end 102 has a handle 108 shaped to be grasped by a surgeon, and the distal end 444 has a retention interface 450 having a recess 452.

The instrument 440 is designed to operate in conjunction with a delivery instrument 460 to implant (i.e., insert and secure) a repair member 462 that has been inserted into the lateral meniscus 64 from a position anteriorly of the tear 72 by a method somewhat similar to that employed in FIGS. 4 and 5. The recess 452 is shaped to manipulate ends of the repair member 462 to keep them from sliding back into the lateral meniscus 64. The delivery instrument 460 may operate to insert the repair member 462 into the lateral meniscus 64 from a position anterior to the tear 72. The delivery instrument 460 has a proximal end 464 designed to be grasped by a surgeon, and a distal end 466 capable of retaining the repair member 462 until insertion is complete.

The repair member 462 may have a first end 472 and a second end 474 designed to be driven into the tissue of the lateral meniscus 64 by the delivery instrument 460. The repair member 462 includes a length of suture 476 and a pair of flip anchors 478 pivotably secured to the ends of the length of suture 476. Each of the flip anchors 478 has a generally elongated shape so that each flip anchor 478 has a narrow profile when rotated into an orientation parallel to the adjoining portion of the suture 476, but forms a significant blockage to suture motion when rotated perpendicular to the adjoining portion of the suture 476. The repair member 462 has a central portion 480 that extends between the first and second ends 472, 474.

In operation, the distal end 444 of the instrument 440 is first inserted through the LMCT 88 until the distal end 444 is positioned posteriorly of the tear 72. The repair member 462 is then inserted into the lateral meniscus 64 in such a manner that the ends 472, 474 pass through the tear 72, through the remainder of the lateral meniscus 64, and through the interior wall of the LMCT 88. As mentioned previously, the delivery instrument 460 may be used to insert the repair member 462 into the lateral meniscus 64.

After the repair member 462 has been inserted as described above, the ends 472, 474 protrude into the LMCT 88. The flip anchors 478 are accessible within the LMCT 88, and are rotated by moving the distal end 444 to place each of the flip anchors 478 within the recess 452, and then moving the distal end 444 in the direction required to induce rotation of the flip anchor 478 into an orientation generally perpendicular to the adjoining portion of the suture 476. In such an orientation, the flip anchors 478 are unable to slide back through the interior wall of the LMCT 88, and back into the lateral meniscus 64. After the repair member 462 has been secured, the instrument 440 may be withdrawn from the LMCT 88. The repair member 462 remains in the knee 10, and is therefore biocompatible, and may also be bioabsorbable, if desired.

Figure 18B:
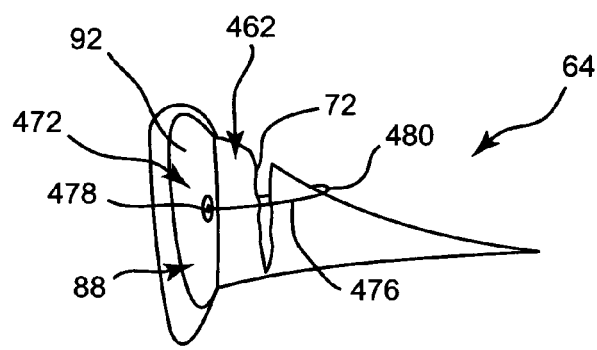
FIG. 18B is a lateral section view of the meniscus and the repair member of FIG. 18A.

Referring to FIG. 18B, a lateral section view illustrates the lateral meniscus 64 and the repair member 462 of FIG. 18A. The central portion 480 of the repair member 462 passes redundantly through the tear 72, and the tension in the repair member 462 keeps the flip anchors 478 oriented perpendicular to the adjoining portions of the suture 476, and keeps the tear 72 closed to permit healing.

Figure 19A:
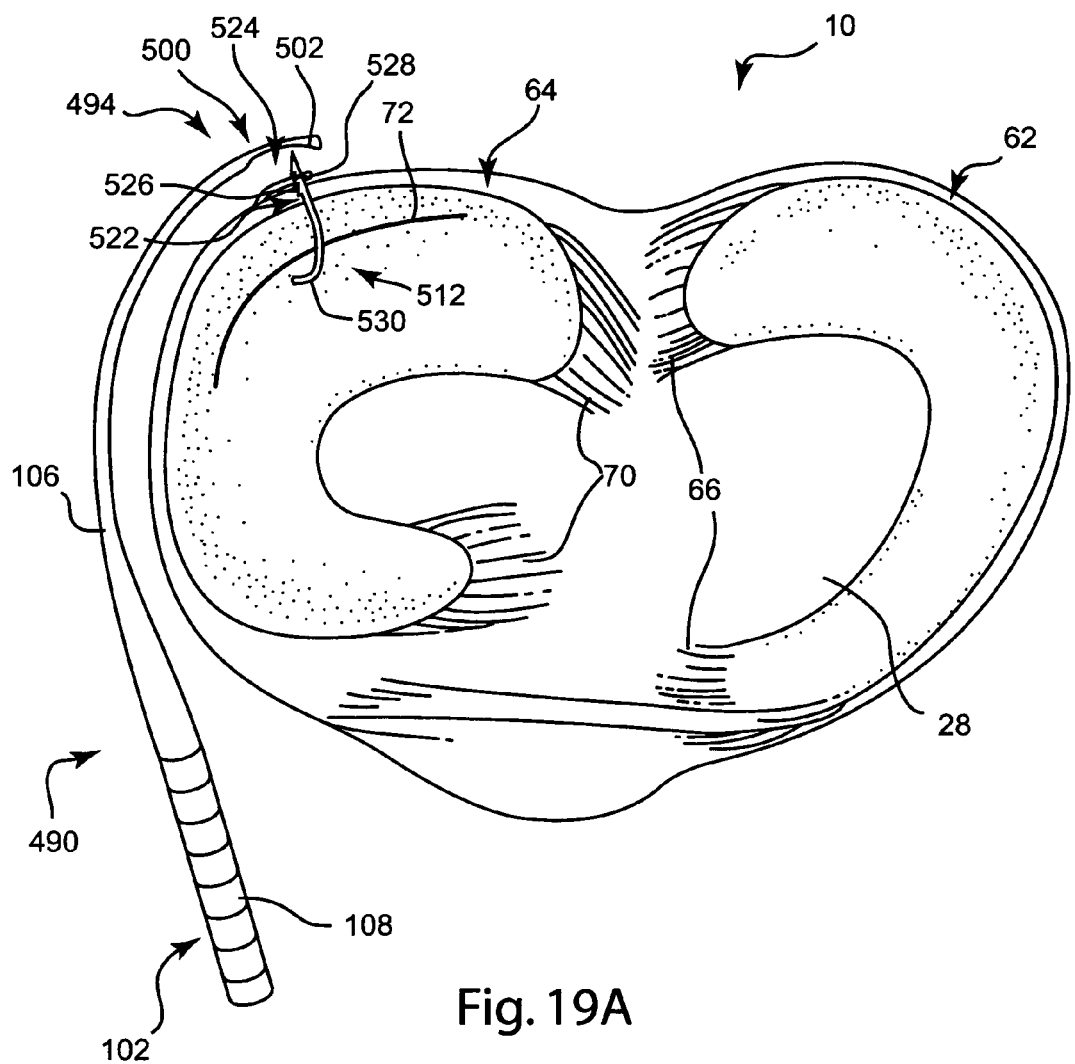
FIG. 19A is a cephalad section view of the knee, showing a repair member in the form of a flexible member having a barbed end and an aperture through which the barbed end passes within the meniscal capsular tunnel to secure the repair member, wherein the repair member redundantly bridges the meniscal tear.

Referring to FIG. 19A, a cephalad section view of the knee 10 illustrates a repair system according to another alternative embodiment of the invention. As shown, a delivery and securement instrument 490, or instrument 490, may have a proximal end 102, a distal end 494, and an intermediate portion 106 that spans the displacement between the proximal and distal ends 102, 494. The proximal end 102 has a handle 108 shaped to be grasped by a surgeon, and the distal end 494 has a delivery interface 500 having a recess 502.

The instrument 490 is designed to insert a repair member 512 into the lateral meniscus 64. The repair member 512 may have a first end 522 and a second end 524. The first end 522 has barbs 526 shaped to be driven into the tissue of the lateral meniscus 64 by the delivery interface 500. The second end 524 has an aperture 528 sized to receive at least one of the barbs 526 of the first end 522, also through the use of the delivery interface 500, which acts as a retention interface as well as a delivery interface. The repair member 512 also has a central portion 530 that extends between the first and second ends 522, 524.

The recess 502 is shaped to retain the second end 524. The repair member 512 may be pre-formed with a curved shape so that the central portion 530 and the first end 522 protrude away from the recess 502 when the second end 524 is retained within the recess 502. In operation, the repair member 512 may first be coupled to the recess 502. The distal end 494 of the instrument 490 may be inserted into and through the LMCT 88 in a manner similar to that of the distal end 104 of the instrument 100. When the distal end 494 and the repair member 512 are positioned posteriorly of the tear 72, the distal end 494 may be urged anteriorly to insert the barbs 526 into the tissue of the lateral meniscus 64 until the barbs 526 have passed through the tear 72 and the central portion 530 is pressed relatively tightly against the interior surface of the LMCT 88.

The curved shape of the repair member 512 may be selected such that, after the barbs 526 have passed through the tear 72, further actuation causes the barbs 526 to pass out of the lateral meniscus 64 on the proximal side, and then to move posteriorly back through the interior wall of the LMCT 88. In the alternative, an instrument (not shown) may be inserted into the knee 10 and used to grasp and/or push the first end 522 to urge the barbs 526 to pass out of the lateral meniscus 64 on the proximal side, and then to move posteriorly back through the interior wall of the LMCT 88. In either case, the distal end 494 may then be further maneuvered to insert the barbs 526 into the aperture 528 until the barbs 526 have moved far enough to be retained within the aperture 528. The distal end 494 may then be moved posteriorly to dislodge the second end 524 from the recess 502. After the repair member 512 has been inserted and secured, the instrument 490 may be withdrawn from the LMCT 88.

Figure 19B:
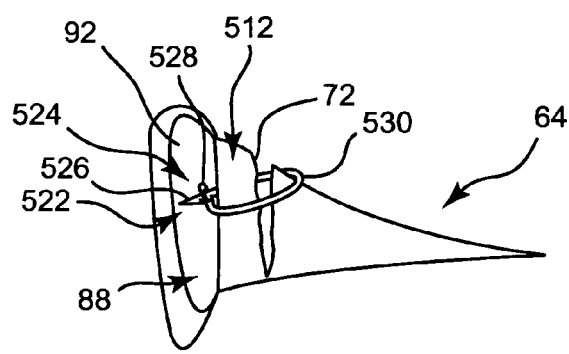
FIG. 19B is a lateral section view of the meniscus and repair member FIG. 19A.

Referring to FIG. 19B, a lateral section view illustrates the lateral meniscus 64 and the repair member 512 of FIG. 19A. The central portion 530 of the repair member 362 passes through the tear 72 and over the proximal face of the lateral meniscus 64. Tension in the repair member 512 keeps the barbs 528 securely seated in place, and keeps the tear 72 closed to permit healing.

Figure 20A:
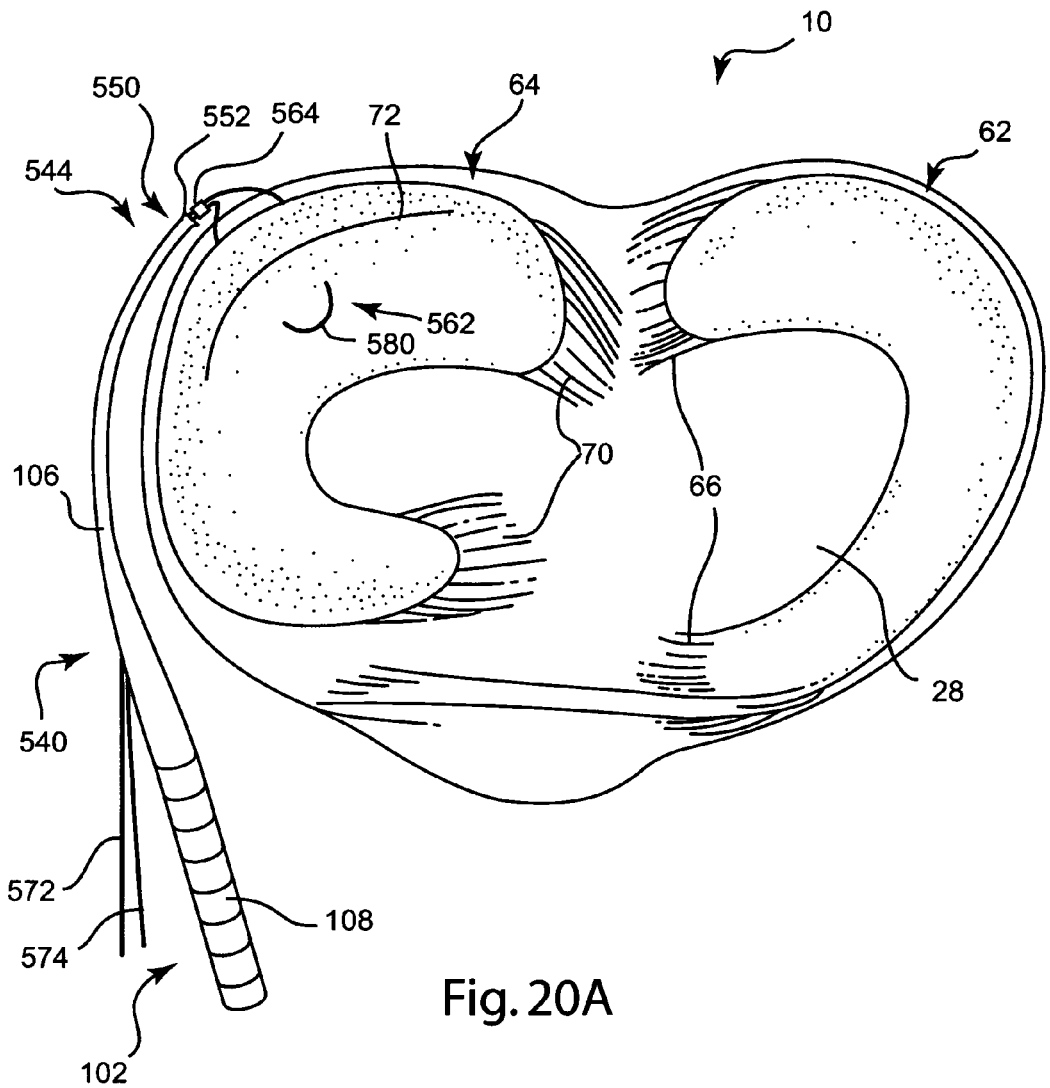
FIG. 20A is a cephalad section view of the knee, showing a repair member in the form of a loop of suture with a suture securing device in the meniscal capsular tunnel and a portion of the loop redundantly bridging the meniscal tear, with another portion of the loop positioned proximally of the meniscus.

Referring to FIG. 20A, a cephalad section view of the knee 10 illustrates a repair system according to yet another alternative embodiment of the invention. As shown, a securement instrument 540, or instrument 540, has a proximal end 102, a distal end 544, and a central portion 106 that spans the displacement between the proximal and distal ends 102, 544. The proximal end 102 has a handle 108 shaped to be grasped by a surgeon, and the distal end 544 has a retention interface 550 having a shoulder 552.

The instrument 540 is designed to secure a repair member 562 in the form of a suture that has been inserted into the lateral meniscus 64, for example, through the use of a delivery instrument such as the delivery instrument 120 of FIGS. 4 and 5. The repair member 562 is secured via a coupling member 564, which may be a line lock such as any of those described in U.S. application Ser. Nos. 10/459,375, 10/936,376, and 11/001,866, which are incorporated herein by reference. According to alternative embodiments, the coupling member 564 have any configuration designed to be movable along the repair member 562 and locked in place at the proper position with respect to the repair member 562.

Steps such as those discussed in connection with FIGS. 3 through 5 may be used to insert the repair member 562 into the tissue of the lateral meniscus 64, withdraw barbed ends (not shown) of the repair member 562 from the LMCT 88, and cut the barbed ends to provide first and second ends 572, 574 of the repair member 562. The repair member 562 also has a central portion 580 that extends between the first and second ends 572, 574.

The coupling member 564 is designed to allow end first and second ends 572, 574 to pass therethrough along only one direction. Once the ends 572, 574 have been routed through the coupling member 564, the coupling member 564 can move along the repair member 562 toward the central portion 580, but not toward the ends 572, 574. The instrument 540 is used to push the coupling member 564 toward the central portion 580 in a manner similar to usage of the push rod 150 to push the knot 164 in FIG. 6.

The shoulder 552 of the retention interface 550 is shaped to abut the adjacent surface of the coupling member 564. One or two terminal apertures (not visible) may be formed in the shoulder 552 to receive the first and second ends 572, 574. The first and second ends 572, 574 may exit the distal end 544 via one or two peripheral apertures (not visible) so that they can be held stationary by a surgeon while the coupling member 564 is pushed toward the central portion 580.

In operation, the repair member 562 may first be inserted into the lateral meniscus 64, for example, through the use of a delivery instrument such as the delivery instrument 120 of FIGS. 4 and 5. The ends of the repair member 562 are withdrawn through the LMCT 88, for example, via an instrument such as the instrument 100 of FIGS. 3 through 5. The anchors are cut away from the repair member 562 to provide the first and second ends 572, 574, which are routed through the coupling member 564.

The first and second ends 572, 574 are passed through the terminal aperture(s) and the peripheral aperture(s) of the distal end 544. Then, the distal end 544 is moved along the LMCT 88, toward the posterior portion 92 to push the coupling member 564 until the coupling member 564 is tightened against the interior wall of the LMCT 88. After the repair member 552 has been inserted and secured, the instrument 540 may be withdrawn from the LMCT 88, and the first and second ends 572, 574 may be cut off adjacent to the coupling member 564.

Figure 20B:
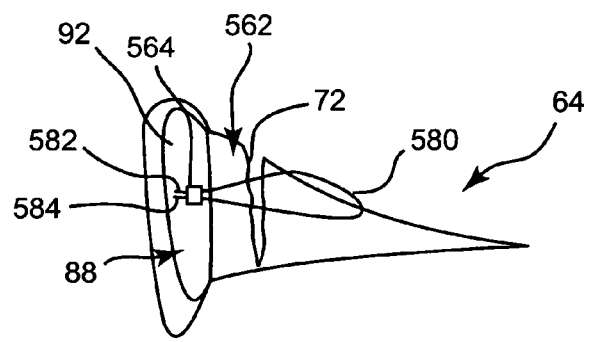
FIG. 20B is a lateral section view of the meniscus and the repair member of FIG. 20A.

Referring to FIG. 20B, a lateral section view illustrates the lateral meniscus 64, the repair member 562, and the coupling member 564 of FIG. 20A. The central portion 580 of the repair member 562 passes redundantly through the tear 72. Tension in the repair member 562 keeps the coupling member 564 securely in place, and keeps the tear 72 closed to permit healing.

The present invention may be embodied in other specific forms without departing from its spirit or essential characteristics. As such, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. A method of repairing a damaged meniscus of a knee, the method comprising:
   inserting a repair member into an anterior portion of a meniscal capsular tunnel of the knee;
   actuating the repair member from a position anterior to the meniscus either medially or laterally around at least a portion of the meniscus to position at least a first end of the repair member posteriorly of the meniscus, within the meniscal capsular tunnel; and
   passing the first end from the meniscal capsular tunnel through at least a portion of the meniscus.

2. The method of claim 1, wherein the repair member comprises a first end having a barbed shape, the method further comprising securing the first end with the barbed shape in response to passage of the first end through at least a portion of the meniscus.

3. The method of claim 1, further comprising coupling the repair member to a delivery interface of an instrument, wherein actuating the repair member around at least a portion of the meniscus comprises urging a distal end of the instrument around at least a portion of the meniscus, wherein passing the first end from the meniscal capsular tunnel through at least a portion of the meniscus comprises actuating the delivery interface to urge the first end into the meniscus.

4. The method of claim 3, wherein actuating the repair member around at least a portion of the meniscus comprises pressing the distal end against tissues within the knee to dilate a potential space between tissues to form the meniscal capsular tunnel.

5. A method of repairing a damaged meniscus of a knee, the method comprising:
   passing a first end of a first repair member through at least a portion of the meniscus;
   inserting an instrument into an anterior portion of a meniscal capsular tunnel of the knee;
   actuating the instrument from a position anterior to the meniscus either medially or laterally around at least a portion of the meniscus to position at least a distal end of the instrument posteriorly of the meniscus, within the meniscal capsular tunnel;
   manipulating the first end with the distal end within a meniscal capsular tunnel of the knee; and
   securing the first repair member to the meniscus in response to manipulation of the first end of the first repair member.

6. The method of claim 5, wherein the repair member comprises a second end, wherein securing the repair member to the meniscus comprises securing the first and second ends together.

7. The method of claim 5, wherein, after passage of the first end through at least a portion of the meniscus, the first end protrudes from the meniscus, wherein securing the repair member comprises preventing withdrawal of the end into the meniscus.

8. The method of claim 5, wherein passing the first end through at least a portion of the meniscus comprises inserting the first end from a location anteriorly of a tear to be repaired.

9. The method of claim 5, wherein the repair member comprises a clip comprising first and second ends, wherein securing the repair member comprises securing the first end to the second end.

10. The method of claim 5, wherein inserting the instrument into the meniscal capsular tunnel comprises pressing the distal end against tissues within the knee to dilate a potential space between the tissues to form the meniscal capsular tunnel.

11. The method of claim 10, further comprising actuating the distal end from an anterior portion of the meniscal capsular tunnel to a posterior portion of the meniscal capsular tunnel, wherein manipulating the first end comprises manipulating the first end within the posterior portion.

12. A method of repairing a damaged meniscus of a knee, the method comprising:
   pressing a distal end of an instrument against tissues within the knee to dilate a potential space between the tissues anteriorly of the meniscus to permit passage of the distal end posterior to the meniscus;
   actuating the instrument from a position anterior to the meniscus either medially or laterally around at least a portion of the meniscus to position at least the distal end of the instrument posteriorly of the meniscus, within a meniscal capsular tunnel;

inserting a first end of a repair member through at least a portion of the meniscus from a position exteriorly of a tear positioned posteriorly, medially, or laterally on the meniscus; and securing the first end to substantially prevent withdrawal of the repair member from the meniscus during normal operation of the knee to expedite reparation of the tear;

wherein the steps of inserting the first end of the repair member through at least a portion of the meniscus and securing the repair member are carried out without requiring retraction of ligamentomuscular structures positioned exteriorly of the tear.

13. The method of claim 12, wherein inserting the first end through at least a portion of the meniscus comprises:

coupling the repair member to a delivery interface of an instrument; and actuating the delivery interface to urge the first end through at least a portion of the meniscus from a position posteriorly of the meniscus.

14. The method of claim 12, wherein securing the first end comprises manipulating the first end with a retention interface of an instrument from a position posteriorly of the meniscus.

\* \* \* \* \*

UNITED STATES PATENT AND TRADEMARK OFFICE
CERTIFICATE OF CORRECTION

PATENT NO. : 7,594,922 B1  Page 1 of 1
APPLICATION NO. : 11/102027
DATED : September 29, 2009
INVENTOR(S) : E. Marlowe Goble, Daniel F. Justin and T. Wade Fallin It is certified that error appears in the above-identified patent and that said Letters Patent is hereby corrected as shown below:

Column 12, Line 9, "FIG. 170" should be changed to --FIG. 7--; Line 18, "242" should be changed to --222--; Line 20, "242" should be changed to --222-- and "246" should be changed to --226--; Line 21, "246" should be changed to --226--; Line 24, "246" should be changed to --226--; Line 27, "242" should be changed to --222--; Line 34, "246" should be changed to --226--; Line 42, "242" should be changed to --222--; Line 43, "246" should be changed to --226--; Line 45, "246" should be changed to --226--.

Column 15, Line 3, "262" should be changed to --312--.

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,594,922 B1 | Page 1 of 1 |
| APPLICATION NO. | : 11/102027 | |
| DATED | : September 29, 2009 | |
| INVENTOR(S) | : Goble et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1098 days.

Signed and Sealed this

Twenty-eighth Day of September, 2010

David J. Kappos
*Director of the United States Patent and Trademark Office*